US006590115B2

(12) United States Patent
Boaz et al.

(10) Patent No.: US 6,590,115 B2
(45) Date of Patent: Jul. 8, 2003

(54) PHOSPHINO-AMINOPHOSPHINES

(75) Inventors: Neil Warren Boaz, Kingsport, TN (US); Sheryl Davis Debenham, Scotch Plains, NJ (US)

(73) Assignee: Eastman Chemical Company, Kingsport, TN (US)

( * ) Notice: Subject to any disclaimer, the term of this patent is extended or adjusted under 35 U.S.C. 154(b) by 27 days.

(21) Appl. No.: 09/957,380

(22) Filed: Sep. 20, 2001

(65) Prior Publication Data

US 2002/0065417 A1 May 30, 2002

Related U.S. Application Data

(60) Provisional application No. 60/264,411, filed on Jan. 26, 2001, and provisional application No. 60/236,564, filed on Sep. 29, 2000.

(51) Int. Cl.[7] .......................... C07F 17/02; B01J 31/00; C07C 5/03
(52) U.S. Cl. .......................... 556/22; 556/144; 556/148; 502/162; 585/276; 568/846
(58) Field of Search .......................... 556/22, 144, 148; 502/162; 585/276; 568/846

(56) References Cited

U.S. PATENT DOCUMENTS 5,760,264 A    6/1998   Brieden .................... 556/22

FOREIGN PATENT DOCUMENTS

| DE | 199 18 420 | 10/2000 |
| WO | WO 02/26695 A2 * | 4/2002 |
| WO | WO 02/26705 A2 * | 4/2002 |
| WO | WO 02/26750 A2 * | 4/2002 |

OTHER PUBLICATIONS

Richards et al, Tetrahedron: Asymmetry, 1998, vol. 9, pp. 2377–2407.
Fiorini et al, Journal of Molecular Catalysis, 1979, vol. 5, pp. 303–310.
Pracejus et al, Tetrahedron Letters, 1977, vol. 39, pp. 3497–3500.
Marquarding et al, Journal of the American Chemical Society, 1970, vol. 92, pp. 5389–5393.
Armstrong et al, Analytical Chemistry, 1985, vol. 57, No. 2, pp. 481–484.
Boaz, Tetrahedron Letters, 1989, vol. 30, No. 16, pp. 2061–2064.
Hayashi et al, Bull Chemical Society of Japan, 1980, vol. 53, No. 4, pp. 1138–1151.
Schmidt et al, Synthesis, 1992, pp. 487–490.
Faure et al, Tetrahedron, 1997, vol. 53, No. 34, pp. 11577–11594.
Müenzenberg et al, Journal of Molecular Structure, 1998, vol. 444, pp. 77–90.
Slugovc et al, Organometallics, 1999, No. 18, pp. 3865–3872.
Aucott et al, Journal of Organometallic Chemistry, 1999, vol. 582, No. 1, pp. 83–89.
Argouarch et al, European Journal of Organic Chemistry, 2000, pp. 2893–2899.
Carpentier et al, Tetrahedron:Asymmetry, 1995, vol. 6, No. 1, pp. 39–42.
Simons et al, Tetrahedron:Asymmetry 1995, vol. 6, No. 2, pp. 505–518.
White et al, Journal of Organic Chemistry, 1999, vol. 64, pp. 7891–7884.
Francio et al, Angew. Chem. Int. Ed., 2000, vol. 39, No. 8, pp. 1428–1430.
Yonehara et al, Journal of Organic Chemistry, 1999, vol. 64, No. 26, pp. 9381–9385.

* cited by examiner

*Primary Examiner*—Porfirio Nazario-Gonzalez
(74) *Attorney, Agent, or Firm*—Michael J. Blake; Bernard J. Graves, Jr.

(57) ABSTRACT

Disclosed are substantially enantiomerically pure bis-phosphine compounds comprising a substantially enantiomerically pure chiral backbone linking two phosphine residues wherein one of the phosphine residues has three phosphorus-carbon bonds and the other phosphine residue has two phosphorus-carbon bonds and one phosphorus-nitrogen bond wherein the nitrogen is part of the chiral backbone. The compounds, which have exhibited surprising air stability, are useful as ligands for metal catalysts for asymmetric reactions and have demonstrated excellent results, in particular as rhodium complexes for asymmetric hydrogenation of enamide, itaconate, and α-ketoester compounds. Also disclosed are novel processes for the preparation of the bis-phosphine compounds and novel intermediate compounds useful in the preparation of the bis-phosphine compounds.

31 Claims, No Drawings

PHOSPHINO-AMINOPHOSPHINES

CROSS REFERENCE TO RELATED APPLICATION

This application claims the benefit of U.S. Provisional Applications Ser. No. 60/236,564, filed Sep. 29, 2000, and Ser. No. 60/264,411, filed Jan. 26, 2001.

FIELD OF THE INVENTION

This invention pertains to novel, substantially enantiomerically pure bis-phosphine compounds possessing the unique feature of having both a carbon-bonded phosphine and a nitrogen-bonded phosphine connected by a divalent chiral group. The compounds are useful as ligands for metal catalysts for asymmetric reactions and have demonstrated surprising stability as well as excellent results, in particular as rhodium complexes for asymmetric hydrogenation. This invention also pertains to novel processes and intermediate compounds useful for the preparation of the bis-phosphine compounds and to compounds comprising one or more of the bis-phosphine compounds in complex association with one or more Group VIII metals and their use for asymmetric hydrogenation.

BACKGROUND OF THE INVENTION

Asymmetric catalysis is the most efficient method for the generation of products with high enantiomeric purity, as the asymmetry of the catalyst is multiplied many times over in the generation of the chiral product. These chiral products have found numerous applications as building blocks for single enantiomer pharmaceuticals as well as in some agrochemicals. The asymmetric catalysts employed can be enzymatic or synthetic in nature. The latter types of catalyst have much greater promise than the former due to much greater latitude of applicable reaction types. Synthetic asymmetric catalysts are usually composed of a metal reaction center surrounded by an organic ligand. The ligand usually is generated in high enantiomeric purity, and is the agent inducing the asymmetry. These ligands are, in general, difficult to make and therefore expensive.

As is described by Richards, C. J.; Locke, A. J. *Tetrahedron: Asymmetry* 1998, 9, 2377–2407, asymmetric ferrocene derivatives have found great utility as ligands for asymmetric catalysis in reactions as varied as asymmetric hydrogenations, asymmetric Aldol reactions, asymmetric organometallic additions, and asymmetric hydrosilations. These ferrocene species usually are bidentate in nature, using a variety of ligating species. In the cases where the ligands are phosphines they invariably are carbon-linked phosphines. In no cases do these ferrocene-based ligands have heteroatom linkage to the phosphorus atom. Fiorini, M. and Giongo, G. M. *J. Mol. Cat.* 1979, 5, 303–310, and Pracejus, G.; Pracejus, H. *Tetrahedron Lett.* 1977, 3497–3500, report that bis-aminophosphine-based asymmetric ligands afford moderate results for asymmetric hydrogenations (<90% enantiomeric excess—ee), but in no cases have these ligands had either a metallocenyl moiety or a mixture of carbon and nitrogen-bonded phosphines included therein. Indeed, there appear to be no reports of chiral, non-racemic, bis-phosphine ligands where one phosphine is bonded to three carbon atoms and the other is bonded to two carbons and one nitrogen.

BRIEF SUMMARY OF THE INVENTION

The novel bis-phosphine compounds provided by our invention are substantially enantiomerically pure bis-phosphine compounds comprising a substantially enantiomerically pure chiral backbone linking two phosphine residues wherein one of the phosphine residues has three phosphorus-carbon bonds and the other phosphine residue has two phophorus-carbon bonds and one phosphorus-nitrogen bond wherein the nitrogen is part of the chiral backbone. These compounds are the first examples of chiral bis-phosphines combining a tri-hydrocarbylphosphine with a dihydrocarbylaminophosphine. These species can be utilized as bidentate ligands for asymmetric catalysis for a variety of reactions. They are of particular interest for asymmetric hydrogenations, and as the rhodium complex they have afforded hydrogenation products with high enantiomeric excess, in particular for the rhodium-catalyzed hydrogenation of prochiral olefins and ketones. The activity of these compounds is readily modified by the choice of the amine substituents.

DETAILED DESCRIPTION

We have discovered a broad group of novel substantially enantiomerically pure bis-phosphine compounds comprised of one phosphine residue having three phosphorus-carbon bonds and the other having two phosphorus-carbon bonds and one phosphorus-nitrogen bond. Examples of the substantially enantiomerically pure, i.e., an enantiomeric excess of 90% or greater, compounds include phosphinometallocenylaminophosphines having the general formulas 1 and 2 (the enantiomer of 1):

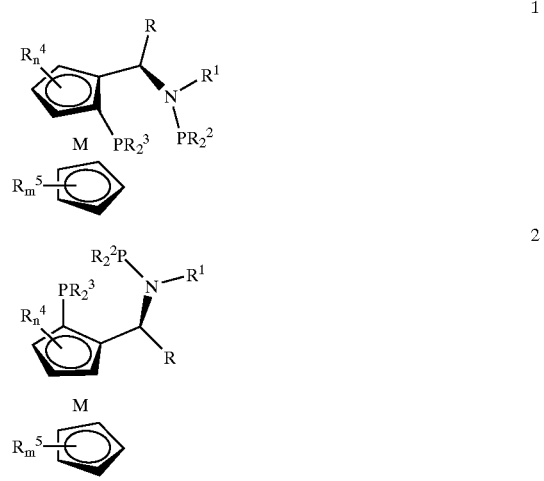

wherein

R is selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

The alkyl groups which may be represented by each of R, $R^1$, $R^2$, $R^3$, $R^4$, and $R^5$ may be straight- or branched-chain, aliphatic hydrocarbon radicals containing up to about 20 carbon atoms and may be substituted, for example, with one to three groups selected from $C_1$–$C_6$-alkoxy, cyano, $C_2$–$C_6$-alkoxycarbonyl, $C_2$–$C_6$-alkanoyloxy, hydroxy, aryl and halogen. The terms "$C_1$–$C_6$-alkoxy", "$C_2$–$C_6$-alkoxycarbonyl", and "$C_2$–$C_6$-alkanoyloxy" are used to denote radicals corresponding to the structures —$OR^6$, —$CO_2$ $R^6$, and —$OCOR^6$, respectively, wherein $R^6$ is $C_1$–$C_6$-alkyl or substituted $C_1$–$C_6$-alkyl. The term "$C_3$–$C_8$-cycloalkyl" is used to denote a saturated, carbocyclic hydrocarbon radical having three to eight carbon atoms. The aryl groups which each of R, $R^1$, $R^2$, $R^3$, $R^4$, and $R^5$ may represent may include phenyl, naphthyl, or anthracenyl and phenyl, naphthyl, or anthracenyl substituted with one to three substituents selected from $C_1$–$C_6$-alkyl, substituted $C_1$–$C_6$-alkyl, $C_6$–$C_{10}$ aryl, substituted $C_6$–$C_{10}$ aryl, $C_1$–$C_6$-alkoxy, halogen, carboxy, cyano, $C_1$–$C_6$-alkanoyloxy, $C_1$–$C_6$-alkylthio, $C_1$–$C_6$-alkylsulfonyl, trifluoromethyl, hydroxy, $C_2$–$C_6$-alkoxycarbonyl, $C_2$–$C_6$-alkanoylamino and —O—$R^7$, S—$R^7$—$SO_2$—$R^7$, —$NHSO_2R^7$ and —$NHCO_2R_7$, wherein $R^7$ is phenyl, naphthyl, or phenyl or naphthly substituted with one to three groups selected from $C_1$–$C_6$-alkyl, $C_6$–$C_{10}$ aryl, $C_1$–$C_6$-alkoxy and halogen.

The heteroaryl radicals include a 5- or 6-membered aromatic ring containing one to three heteroatoms selected from oxygen, sulfur and nitrogen. Examples of such heteroaryl groups are thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heteroaryl radicals may be substituted, for example, with up to three groups such as $C_1$–$C_6$-alkyl, $C_1$–$C_6$-alkoxy, substituted $C_1$–$C_6$-alkyl, halogen, $C_1$–$C_6$-alkylthio, aryl, arylthio, aryloxy, $C_2$–$C_6$-alkoxycarbonyl and $C_2$–$C_6$-alkanoylamino. The heteroaryl radicals also may be substituted with a fused ring system, e.g., a benzo or naphtho residue, which may be unsubstituted or substituted, for example, with up to three of the groups set forth in the preceding sentence. The term "halogen" is used to include fluorine, chlorine, bromine, and iodine.

The compounds of the invention which presently are preferred have formulas 1 and 2 wherein R is $C_1$ to $C_6$ alkyl; $R^1$ is hydrogen or $C_1$ to $C_6$ alkyl; $R^2$ is aryl (preferably phenyl), ethyl, isopropyl, or cyclohexyl; $R^3$ is aryl, most preferably phenyl; $R^4$ and $R^5$ are hydrogen; and M is iron, ruthenium, or osmium, most preferably iron.

The compounds of our invention contain both a carbon-linked and a nitrogen-linked phosphine. This mixture of features is not known in the literature (and is particularly not known for metallocene-based ligands) and affords a different electronic environment when complexed to a catalyst metal center as compared to other ligands. In addition, the metallocene-based ligands are readily modifiable by varying $R^1$ according to the choice of the amine used, and thus allow simple modification of the reactivity and selectivity of the catalyst prepared from these ligands. An unexpected but particularly advantageous characteristic of this metallocene-based phosphino-aminophosphine structural class is their resistance to oxidative degradation. Indeed, these types of compounds retain activity and enantioselectivity (as demonstrated by both physical properties and trial reactions of their metal complexes) over extended periods at ambient temperature in an air atmosphere, conditions under which many phosphines oxidize to the inactive phosphine oxides.

Our invention also provides novel processes for the preparation of compounds of formulas 1 and 2. Thus, one embodiment of the processes of the present invention involves a process for the preparation of a substantially enantiomerically pure compound having formula 1:

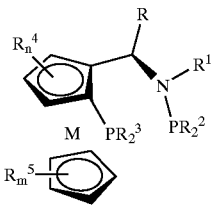

1 which comprises the steps of:

(1) contacting a dialkyl amine having formula 3:

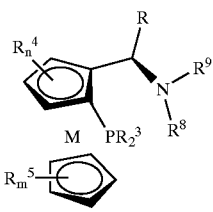

3 with a carboxylic anhydride having the formula $(R^{10}CO)_2O$ to obtain an ester compound having formula 4:

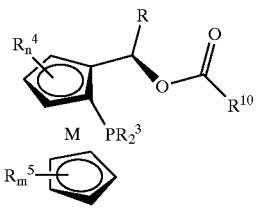

4

(2) contacting the ester produced in step (1) with an amine having the formula $H_2N$—$R^1$ to obtain an intermediate amino-phosphine compound having formula 5:

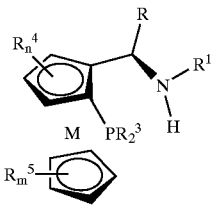

5

(3) contacting intermediate compound 5 with a halophosphine having the formula X—$P(R^2)_2$;

wherein R, $R^1$, $R^2$, $R^3$, $R^4$, $R^5$, n, m, and M are defined hereinabove, $R^8$ and $R^9$ are independently selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen, $R^{10}$ is a $C_1$ to $C_4$ alkyl radical, and X is chlorine, bromine, or iodine. The compounds of formula 2 may be prepared when dialkylamine having formula 6:

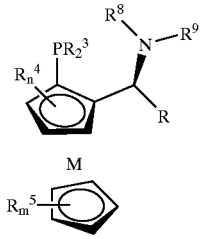

is used as the starting material affording intermediates 7 and 8 analogous to 4 and 5, respectively.

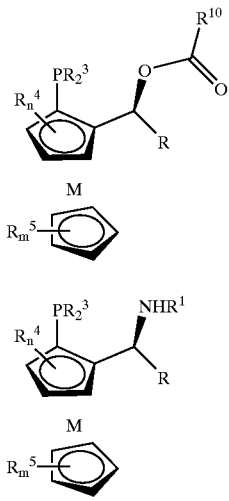

In the first step of the process, dialkylamine reactant compound 3 is contacted with a carboxylic anhydride. The amount of anhydride used may be about 1 to 100 moles, preferably about 2 to 10 moles, per mole of dialkylamine reactant 3. Although the carboxylic anhydride may contain up to about 8 carbon atoms, acetic anhydride is particularly preferred. The first step of the process may be carried out at a temperature between about 20° C. and the boiling point of the anhydride, preferably about 80 to 120° C. While an inert solvent may be used in step (1), such a solvent is not essential and the carboxylic anhydride may function as both solvent and reactant. At the completion of the first step, the ester intermediate may be isolated for use in the second step by conventional procedures such as crystallization or removing the carboxylic anhydride and any extraneous solvent present, e.g., by distillation.

Dialkylamine reactant compounds 3 can be prepared in high enantiomeric purity by several known methods. For example, precursor 9 having the formula:

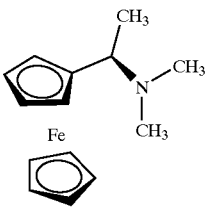

can be prepared in high enantiomeric purity using the procedures described by Marquarding, D.; Klusacek, H.; Gokel, G.; Hoffmann, P.; Ugi, I. *J. Am. Chem. Soc.* 1970, 92, 5389–5393; Armstrong, D. W.; DeMond, W.; Czech, B. P. *Anal. Chem.* 1985, 57, 481–484; and Boaz, N. W. *Tetrahedron Letters* 1989, 30, 2061–2064. Precursor 9 then can be converted by known procedures to dialkylamine reactant 3, e.g., using the procedures described in Hayashi, T. et al. *Bull Chem. Soc. Jpn.* 1980, 53, 1130–1151; and the references mentioned in the preceding sentence. The enantiomeric species 6 can be prepared in a like manner.

In the second step of the process, the ester intermediate obtained from step (1) is contacted and reacted with an amine having the formula $H_2NR^1$ in the presence of a $C_1$ to $C_4$ alkanol solvent, preferably methanol or 2-propanol. The second step may be carried out at a temperature between 20° C. and the boiling point of the solvent, preferably about 25 to 50° C. The mole ratio of the amine:ester intermediate 4 (or 7) typically is in the range of about 1:1 to 25:1. Intermediate 5 (or 8) may be recovered for use in step (3) by conventional procedures such as extractive purification or crystallization.

In the third step of our novel process, intermediate 5 (or 8) is contacted and reacted with a halophosphine of the formula $XPR^2_2$ wherein X is chlorine, bromine, or iodine using a halophosphine:intermediate 5 (or 8) mole ratio in the range of about 0.8:1 to 1.3:1. The reaction of step (3) is carried out in the presence of an acid acceptor such as a tertiary amine, e.g., trialkylamines containing a total of 3 to 15 carbon atoms, pyridine, substituted pyridines and the like. The amount of acid acceptor used normally is at least 1 mole of acid acceptor per mole of halophosphine employed and up to 5 moles of acid acceptor per mole of halophosphine. Step (3) is carried out in the presence of an inert solvent. Examples of inert solvents include, but are not limited to, non-polar, aprotic solvents such as aliphatic and aromatic hydrocarbons containing 6 to 10 carbon atoms, e.g., hexane, heptane, octane, toluene, the various xylene isomers and mixtures thereof, and the like; halogenated, e.g., chlorinated, hydrocarbons containing up to about 6 carbon atoms such as dichloromethane, chloroform, tetrachloroethylene, chorobenzene and the like; and cyclic and acyclic ethers containing from about 4 to 8 carbon atoms, e.g., tert-butyl methyl ether, diisopropyl ether, tetrahydrofuran and the like. The acid acceptor and solvent particularly preferred are triethylamine and toluene, respectively. Step (3) may be carried out at a temperature between about −20° C. and the boiling point of the solvent, preferably about 0 to 30° C.

Intermediate amino-phosphine compounds 5 and 8 are novel compounds and constitute an additional embodiment of our invention. Also included within the scope of the present invention are catalytically-active compounds comprising one or more substantially enantiomerically pure, bis-phosphine compounds comprising a substantially enantiomerically pure chiral backbone linking two phosphine residues wherein one of the phosphine residues has three phosphorus-carbon bonds and the other phosphine residue has two phophorus-carbon bonds and one phosphorus-nitrogen bond wherein the nitrogen is part of the chiral backbone in complex association with one or more Group VIII metals, preferably rhodium, iridium or ruthenium.

EXAMPLES

The novel compounds and processes provided by the present invention are further illustrated by the following examples.

Example 1

Preparation of (R)-1-[(S)-2-Diphenylphosphino) ferrocenyl]ethylamine (R,S-5a)($R^1$=H)

(R)-N,N-Dimethyl-1-[(S)-2-(diphenylphosphino) ferrocenyl]ethylamine (R,S-3a, R=$R^8$=$R^9$=methyl, $R^3$=phenyl-Ph, $R^4$=$R^5$=H, M=Fe))(10.0 g; 22.7 mmol) was combined with acetic anhydride (14.25 mL; 150 mmol; 6.7 equivalents) in a 250-mL flask. The flask was evacuated and filled with nitrogen ten times and then heated to 100° C. for 2 hours, at which point thin layer chromatography (tlc) analysis indicated no 3a present. The residual acetic anhydride was evaporated at reduced pressure to afford a solid mass containing acetate ester R,S-4a. A portion (1.0 g) of acetate ester R,S-4a was removed and the remainder was dissolved in isopropanol (200 mL) and treated with concentrated ammonium hydroxide (28% $NH_3$; 24.3 mL; 360 mmol; 17.5 equiv). The reaction mixture was heated to 50° C. overnight to completely consume 4 according to tlc analysis. The mixture was concentrated to small volume at reduced pressure. The residue was dissolved in ethyl acetate and extracted with 10% aqueous citric acid (3×75 mL). The acidic extracts were neutralized with 4 N NaOH (115 mL) to pH 12 and extracted with ethyl acetate (3×50 mL). The combined organic solution was dried with magnesium sulfate and concentrated in vacuo to afford 7.34 g (87% yield) of R,S-5a ($R^1$=hydrogen). S,R-8a was prepared in the same manner from S,R-6a.

$^1$H NMR ($CDCl_3$) δ 7.6–7.2 (m, 10H); 4.43 (br s, 1H); 4.28 (m, 1H); 4.20 (m, 1H); 4.016 (s, 5H); 3.76 (m, 1H); 1.439 (d, 3H, J=6 59 Hz).

Preparation of (S)-N-diphenylphosphino-1-[(R)-2-(diphenylphosphino)-ferrocenyl]ethylamine (S,R-2a) ($R^1$=H)

Amine S,R-8a (1.9 g; 4.6 mmol) was dissolved in 11 mL of toluene. Triethylamine (1.3 mL; 9.3 mmol; 2 equivalents) was added. The mixture was cooled in ice water and degassed with a nitrogen purge for 10 minutes. Chlorodiphenylphosphine (860 µL; 4.8 mmol; 1.04 equivalents) was added dropwise. The reaction mixture was allowed to warm to ambient temperature and stirred overnight to almost completely consume 8a and afford a new spot on tlc. Heptane (11 mL) was added and the reaction mixture was filtered and the precipitate was washed with toluene. The filtrate was concentrated to afford 2a ($R^1$=hydrogen) contaminated with some triethylamine hydrochloride. The crude product was triturated with 1:1 toluene:heptane (20 mL) at 4° C. for 1 hour. The mixture was filtered and the filtrate was concentrated in vacuo to afford 2.6 g of S,R-2a (95% yield) as an oil. R,S-1a was prepared in the same manner from R,S-5a.

$^1$H NMR ($CDCl_3$) δ 7.8–7.1 (m, 20H); 4.50 (m, 1H); 4.46 (br s, 1H); 4.30 (m, 1H); 3.915 (s, 5H); 1.515 (d, 3H, J=6.59 Hz). FDMS: m/z 597.25 ($M^+$). $[\alpha]_D^{25}$+233.30 (c 1.12, toluene).

Example 2

Preparation of (S)-N-Methyl-1-[(R)-2-(diphenylphosphino)-ferrocenyl]ethylamine (S,R-8b) ($R^1$=Me)

(S)-N,N-Dimethyl-1-[(R)-2-(diphenylphosphino) ferrocenyl]ethylamine (S,R-6a)(5.0 g; 11.3 mmol) was combined with acetic anhydride (7.1 mL; 75.2 mmol; 6.7 equivalents) in a 100-mL flask. The flask was evacuated and filled with nitrogen ten times and then heated to 100° C. for 2 hours, at which point tlc analysis indicated no 6a present. The residual acetic anhydride was evaporated at reduced pressure to afford a solid mass containing acetate ester S,R-7a. This material was dissolved in isopropanol (110 mL) and treated with 40% aqueous methylamine (14.6 mL; 170 mmol; 15 equivalents). The reaction mixture was heated to 50° C. for 48 hours to completely consume 7a according to tlc analysis. The mixture was concentrated to small volume at reduced pressure. The residue was dissolved in 1:1 ethyl acetate:heptane and extracted with 10% aqueous citric acid (4×10 mL). The acidic extracts were neutralized with 2 N NaOH (50 mL) and extracted with ethyl acetate (3×20 mL). The combined organic solution was dried with magnesium sulfate and concentrated in vacuo to afford 4.33 g (90% yield) of S,R-8b ($R^1$=methyl) as an orange solid. R,S-5b was prepared in the same manner from R,S-3a.

$^1$H NMR ($CDCl_3$) δ 7.55 (m, 2H); 7.37 (m, 3H); 7.26 (m, 5H); 4.463 (br s, 1H); 4.286 (m, 1H); 4.028 (s, 5H); 3.94 (m, 1H); 3.78 (m, 1H); 1.943 (s, 3H); 1.445 (d, 3H, J=6.59 Hz). FDMS: m/z 427 ($M^+$).

Preparation of (S)-N-Methyl-N-diphenylphosphino-1-[(R)-2-(Diphenylphosphino)ferrocenyl]ethylamine (S,R-2b)($R^1$=Me)

Amine S,R-8b (427 mg; 1.0 mmol) was dissolved in 2.5 mL of toluene. Triethylamine (0.29 mL; 2.1 mmol; 2.1 equiv) was added. The mixture was cooled in ice water and degassed with an argon purge for 10 minutes. Chlorodiphenylphosphine (180 µL; 1.0 mmol; 1.0 equiv) was added dropwise. The reaction mixture was allowed to warm to ambient temperature and stirred overnight to afford almost complete consumption of 8b and a new spot on tlc. Heptane (2.5 mL) was added and the reaction mixture was filtered and the precipitate was washed with heptane. The filtrate was concentrated in vacuo to afford 0.68 g of S,R-2b ($R^1$=methyl) as a yellow foam. R,S-1b was prepared in the same manner from R,S-5b.

$^1$H NMR ($CDCl_3$) δ 7.65 (m, 2H); 7.4–7.0 (m, 14H); 6.82 (m, 4H); 5.006 (m, 1H); 4.502 (br s, 1H); 4.40 (m, 1H); 4.15 (m, 1H); 3.798 (s, 5H); 2.148 (d, 3H, J=3.30 Hz); 1.471 (d, 3H, J=687 Hz). FDMS: m/z 611 ($M^+$). $[\alpha]_D^{25}$+229.80 (c 1.10, toluene)

Example 3

Preparation of (R)-1-[(S)-2-(Diphenylphosphino) ferrocenyl]ethyl acetate (R,S-4a)

(R)-N,N-Dimethyl-1-[(S)-2-(diphenylphosphino) ferrocenyl]-ethylamine(R,S-3a)(10.4 g; 24.0 mmol) was combined with acetic anhydride (15 mL; 136 mmol; 5.7 equiv) in a 100-mL flask. The flask was evacuated and filled with nitrogen ten times and then heated to 100° C. for 2 hours, at which point tlc analysis indicated no 3a present. The residual acetic anhydride was evaporated at reduced pressure to afford acetate R,S-4a. This material could be recrystallized from an ethyl acetate-heptane mixture.

$^1$H NMR (CDCl$_3$) δ 7.52 (m, 2H); 7.37 (m, 3H); 7.3–7.15 (m, 5H); 6.206 (q, 1H, J=2.75 Hz); 4. 568 (m, 1H); 4.349 (m, 1H); 4.045 (s, 5H); 3.800 (m, 1H); 1.630 (d, 3H, J=6.32 Hz); 1.170 (s, 3H). FDMS: m/z 456 (M$^+$).

Preparation of (R)-N-Ethyl-1-[(S)-2-(diphenylphosphino)-ferrocenyl]ethylamine (R,S-5c) (R$^1$=Et)

(R)-1-[(S)-2-(diphenylphosphino)-ferrocenyl]ethyl acetate (R,S-4a) (1.37 g; 3.0 mmol) was slurried in isopropanol (25 mL) and treated with 70% aqueous ethylamine (3.6 mL; 45 mmol; 15 equivalents). The reaction mixture was heated to 50° C. for two days to completely consume 4a according to tlc analysis. The mixture was concentrated to small volume at reduced pressure. The residue was dissolved in 1:1 ethyl acetate:heptane and extracted with 10% aqueous citric acid (2×25 mL). The acidic extracts were neutralized with 4 N NaOH (25 mL) and extracted with ethyl acetate (3×25 mL). The combined organic solution was dried with magnesium sulfate and concentrated in vacuo to afford 1.19 g (90% yield) of R,S-5c (R$^1$=ethyl) as an orange solid. S,R-8c was prepared in the same manner from S,R-7a.

$^1$H NMR (CDCl$_3$) δ 7.6–7.2 (m, 1OH); 4.5 (br s, 1H); 4.28 (m, 1H); 4.05 (s, 5H); 4.0 (m, 1H); 3.78 (m, 1H); 2.4–2.2 (m, 2H); 1.45 (d, 3H); 0.42 (t, 3H).

Preparation of (R)-N-Ethyl-N-diphenylphosphino-1-[(S)-2-(Diphenylphosphino)ferrocenyl]ethylamine (R,S-1c)(R$^1$=Et)

Amine R,S-5c (1.1 g; 2.5 mmol) was dissolved in 6 mL of toluene. Triethylamine (0.69 mL; 5.0 mmol; 2.0 equiv) was added. The mixture was cooled in ice water and degassed with an argon purge for 10 minutes. Chlorodiphenylphosphine (470 μL; 2.6 mmol; 1.05 equiv) was added dropwise. The reaction mixture was allowed to warm to ambient temperature and stirred overnight to afford almost complete consumption of 5c and a new spot on tlc. Heptane (7 mL) was added and the reaction mixture was filtered and the precipitate was washed with toluene and heptane. The filtrate was concentrated and then re-suspended in heptane. This mixture was filtered and concentrated in vacuo to afford 1.41 g (90%) of R,S-1c (R$^1$=ethyl) as a yellow foam. S,R-2c was prepared in the same manner from S,R-8c.

$^1$H NMR (CDCl$_3$) δ 7.7–7.05 (m, 18H); 6.987 (m, 2H); 4.766 (br s, 1H); 4.7 (m, 1H); 4.405 (br s, 1H); 4.139 (br s, 1H); 3.822 (s, 5H); 2.65 (m, 2H); 1.768 (d, 3H, J=6.87 Hz); 0.698 (t, 3H, J=6.87 Hz). FDMS: m/z 625.25 (M$^+$). $[\alpha]_D^{25}$–278.3° (c 1.02, toluene).

Example 4

Preparation of (R)-N-Propyl-1-[(S)-2-(diphenylphosphino)-ferrocenyl]ethylamine (R,S-5d) (R$^1$=Pr)

(R)-1-[(S)-2-(diphenylphosphino)-ferrocenyl]ethyl acetate (R,S-4a)(2.50 g; 5.5 mmol) was dissolved in methanol (45 mL) and treated with n-propylamine (2.2 mL; 26.8 mmol; 4.9 equivalents). The reaction mixture was heated to 50° C. for 2 hours to completely consume 4a according to tlc analysis. The mixture was concentrated to small volume at reduced pressure. The residue was dissolved in 1:1 ethyl acetate:heptane and extracted with 10% aqueous citric acid (3×25 mL). The acidic extracts were neutralized with 4 N NaOH (38 mL) and extracted with ethyl acetate (3×25 mL). Solid was noted in the organic extracts. This was collected by filtration and air-dried to afford 0.58 g of the citric acid salt of R,S-5d (R$^1$=propyl) as orange crystals. The organic solution was dried with magnesium sulfate and concentrated to afford 1.27 g ((51%) of R,S-5d (R$^1$=propyl) as an oil. S,R-8d was prepared in the same manner from S,R-7a.

$^1$H NMR (CDCl$_3$) δ 7.6–7.2 (m, 1OH); 4.497 (br s, 1H); 4.290 (br s, 1H); 4.025 (s, 5H); 3.764 (br s, 1H); 3.205 (q, 1H, J=7.14 Hz); 2.35–2.1 (m, 2H); 1.462 (d, 3H, J=6.59 Hz); 0.9–0.6 (m, 2H); 0.506 (t, 3H, J=7.14 Hz).

Preparation of (R)-N-Propyl-N-diphenylphosphino-1-[(S)-2-(diphenylphosphino)ferrocenyl]ethylamine (R,S-1d) (R$^1$=Pr)

Amine R,S-5d (400 mg; 0.88 mmol) was dissolved in 2.1 mL of toluene. Triethylamine (250 μL; 1.8 mmol; 2.0 equiv) was added. The mixture was cooled in ice water and degassed with an nitrogen purge for 10 min. Chlorodiphenylphosphine (200 μL; 1.1 mmol; 1.25 equiv) was added dropwise. The reaction mixture was allowed to warm to ambient temperature and stirred overnight to afford almost complete consumption of 5d and a new spot on tlc. Heptane (5 mL) was added and the reaction mixture was filtered and the precipitate was washed with toluene and heptane. The filtrate was concentrated in vacuo to afford 0.55 g (86%) of R,S-1d (R$^1$=propyl). S,R-2d was prepared in the same manner from S,R-8d.

$^1$H NMR (CDCl$_3$) δ 7.65 (m, 2H); 7.5–7.1 (m, 16H); 6.95 (m, 2H); 4.75 (br s, 1H); 4.65 (m, 1H); 4.4 (m, 1H); 4.15 (br s, 1H); 3.82 (s, 5H); 2.42 (m, 2H); 1.81 (d, 3H); 1.4–1.2 (m, 2H); 0.39 (t, 3H). FDMS: m/z 639.34 (M$^+$). $[\alpha]_D^{25}$–101.4° (c 1.05, toluene).

Example 5

Preparation of (S)-N-Methyl-N-diethylphosphino-1-[(R)-2-(diphenylphosphino)ferrocenyl]ethylamine (S,R-2e, R$^1$=Me, R$^2$=Et)

Amine S,R-8b (500 mg; 1.17 mmol) was slurried in 5 mL of toluene. Triethylamine (0.33 mL; 2.34 mmol; 2.0 equiv) was added. The mixture was cooled in ice-water and degassed with an argon purge for 15 minutes. Chlorodiethylphosphine (0.17 mL; 1.40 mmol; 1.2 equiv) was added dropwise. The reaction mixture was stirred in ice-water for 30 min to completely consume 8b according to tlc analysis. The reaction mixture was allowed to warm to ambient temperature overnight. Heptane (10 mL) was added and the reaction mixture was filtered and the precipitate was washed with heptane. The filtrate was concentrated in vacuo to afford 0.59 g (98%) of S,R-2e as a yellow foam.

$^1$H NMR (DMSO-d$_6$) δ 7.53 (m, 2H); 7.40 (m, 3H); 7.18 (m, 3H); 6.969 (m, 2H); 4.503 (m, 2H); 4.392 (m, 1H); 3.873 (m, 1H); 3.831 (s, 5H); 1.914 (d, 3H, J=3.02 Hz); 1.438 (d, 3H, J=6.87 Hz); 1.3–1.0 (m, 4H);0.841 (dd, 2H, J=7.42, 15.11 Hz); 0.55–0.4 (m, 2H). FDMS: m/z 515 (M$^+$). $[\alpha]_D^{25}$+328.9° (c 1.01, toluene).

Example 6

Preparation of (R)-N-Methyl-N-diisopropylphosphino-1-[(s)-2-(diphenylphosphino)ferrocenyl]ethylamine (R,S-1f, R$^1$=Me, R$^2$=i-Pr)

Amine R,S-5b (1.00 g; 2.34 mmol) was dissolved in 5 mL of toluene. Triethylamine (0.65 mL; 4.7 mmol; 2.0 equiv)

was added. The mixture was cooled in ice water and degassed with an argon purge for 15 minutes. Chlorodiisopropylphosphine (0.39 mL; 2.46 mmol; 1.05 equiv) was added dropwise. The reaction mixture was allowed to warm to ambient temperature and stirred overnight to afford partial consumption of 5b and a new spot according to tlc analysis. The mixture was heated to 50° C. for 18 hours to afford marginally more conversion. Heptane (10 mL) was added and the reaction mixture was filtered and the precipitate was washed with heptane. The filtrate was concentrated in vacuo and the crude product was filtered through a pad of alumina, eluting with 85:15:5 heptane:ethyl acetate:triethylamine to afford 0.83 g (65%) of R,S-1f as a yellow foam. S,R-2f was prepared in a similar fashion from S,R-8b.

$^1$H NMR (DMSO-$d_6$) δ 7.57 (m, 2H); 7.40 (m, 3H); 7.20 (m, 3H); 7.09 (m, 2H); 4.538 (br s, 1H); 4.436 (m, 1H); 4.31 (m, 1H); 4.04 (br s, 1H); 3.784 (s, 5H); 2.103 (d, 3H, J=2.20 Hz); 1.62 (m, 1H); 1.557 (d, 3H, J=6.87 Hz); 1.34 (m, 1H); 0.85–0.60 (m, 12H). FDMS: m/z 543.40 (M$^+$).

$[\alpha]_D^{25}$ −301.9° (c 1.15, toluene).

Example 7

Preparation of (R)-N-Methyl-N-dicyclohexylphosphino-1-[(S)-2-(diphenylphosphino)ferrocenyl]ethylamine (R,S-1g, R$^1$=Me, R$^2$=c-C$_6$H$_{11}$)

Amine R,S-5b (2.00 g; 4.7 mmol) was dissolved in 10 mL of toluene. Triethylamine (1.30 mL; 9.4 mmol; 2.0 equiv) was added. The mixture was cooled in ice water and degassed with an argon purge for 15 minutes. Chlorodicyclohexylphosphine (1.05 mL; 4.94 mmol; 1.05 equiv) was added dropwise. The reaction mixture was allowed to warm to ambient temperature and stirred overnight to afford partial consumption of 5b and a new spot according to tlc analysis. The mixture was heated to 50° C. for 18 hours to afford significantly more conversion. Heptane (20 mL) was added and the reaction mixture was filtered, the precipitate was washed with heptane, and the combined filtrate and wash were concentrated in vacuo. The crude product was filtered through a pad of alumina, eluting with 85:15:5 heptane:ethyl acetate:triethylamine to afford 1.50 g (52%) of R,S-1g as a yellow foam. S,R-2g was prepared in a similar fashion from S,R-8b.

$^1$H NMR (DMSO-$d_6$) α 7.60 (m, 2H); 7.415 (m, 3H); 7.19 (m, 3H); 7.04 (m, 2H); 4.532 (br s, 1H); 4.442 (m, 1H); 3.312 (m, 1H); 4.112 (br s, 1H); 3.712 (s, 5H); 2.143 (d, 3H, J=1.92 Hz); 1.549 (d, 3H, J=6.87 Hz); 1.7–0.7 (m, 22H). FDMS: m/z 624 (M$^+$). $[\alpha]_D^{25}$ −292.2° (c 1.01, toluene).

The utilization of diphosphine 1 or 2 requires the complexation of the ligand with a catalytically active metal ("metal") which is not the structural metal of the metallocene. The particular metal chosen depends on the desired reaction. There are a large number of possible reactions of a wide variety of substrates using catalysts based on compounds 1 and 2, including but not limited to asymmetric hydrogenations, asymmetric reductions, asymmetric hydroborations, asymmetric olefin isomerizations, asymmetric hydrosilations, asymmetric allylations, and asymmetric organometallic additions. The utility of ligands 1 and 2 will be demonstrated through asymmetric hydrogenation reactions of their metal complexes, which is also an embodiment of our invention. Thus, the present invention includes a process for the hydrogenation of a hydrogenatable compound which comprises contacting the hydrogenatable compound with hydrogen in the presence of a catalyst complex comprising ligands 1 or 2 in complex association with a metal. Although not wishing to be bound to a particular substrate type, the asymmetric hydrogenation of enamide substrates to afford amino acid derivatives is of particular interest in the pharmaceutical industry, and catalysts based on ligands 1 and 2 show particularly high enantioselectivity for these transformations. Enamide compounds that can be hydrogenated under these circumstances contain the residue C=C(N—C=O)—C=O, such that if this residue is present in the hydrogenatable compound the transformation will proceed with high enantioselectivity.

The preferred enamide reactants have the general formula 10,

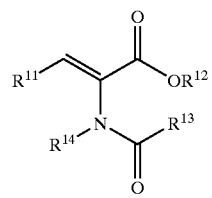

10 wherein
R$^{11}$, R$^{12}$, and R$^{14}$ are independently selected from hydrogen, substituted and unsubstituted, branched- and straight-chain C$_1$ to C$_{20}$ alkyl, substituted and unsubstituted C$_3$ to C$_8$ cycloalkyl, substituted and unsubstituted C$_6$ to C$_{20}$ carbocyclic aryl, and substituted and unsubstituted C$_4$ to C$_{20}$ heteroaryl wherein the heteroatoms are selected from sulfur, nitrogen, or oxygen; and
R$^{13}$ is selected from hydrogen, substituted and unsubstituted C$_1$ to C$_{20}$ alkyl, substituted and unsubstituted C$_1$ to C$_{20}$ alkoxy, substituted and unsubstituted C$_3$ to C$_8$ cycloalkyl, substituted and unsubstituted C$_3$ to C$_8$ cycloalkoxy, substituted and unsubstituted carbocyclic C$_6$ to C$_{20}$ aryl, substituted and unsubstituted carbocyclic C$_6$ to C$_{20}$ aryloxy, substituted and unsubstituted C$_4$ to C$_{20}$ heteroaryl wherein the heteroatoms are selected from sulfur, nitrogen, or oxygen and substituted and unsubstituted C$_4$ to C$_{20}$ heteroaryloxy wherein the heteroatoms are selected from sulfur, nitrogen, and oxygen; or R$^{13}$ and R$^{14}$ collectively represent a substituted or unsubstituted alkylene group of 14 chain carbon atoms forming a lactam.

The enamides reactants having formula 10 can be prepared using the methodology described in Schmidt, U.; Griesser, H.; Leitenberger, V.; Lieberknecht, A.; Mangold, R.; Meyer, R.; Riedl, B. *Synthesis* 1992, 487–490.

The products of the hydrogenation of enamides having formula 10 with catalysts based on ligands 1 and 2 are comprised of species with formula 11,

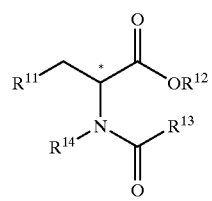

11 wherein R$^{11}$, R$^{12}$, R$^{13}$, and R$^{14}$ are as defined above. These compounds are generally produced with very high enantioselectivity (>90% ee), with the particular enantiomer produced depending upon whether ligand 1 or ligand 2 is used.

Catalysts based on ligands 1 and 2 also show high enantioselectivity for the asymmetric hydrogenation of various itaconate and α-ketoester derivatives. The itaconate compounds which may be selectively hydrogenated have general formula 14,

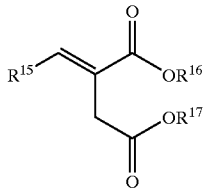

14 wherein $R^{15}$ is selected from hydrogen, substituted and unsubstituted, branched- and straight-chain $C_1$–$C_{20}$ alkyl, and substituted and unsubstituted $C_3$–$C_8$ cycloalkyl, and $R^{16}$ and $R^{17}$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen. The preferred itaconate reactants have formula 14 wherein $R^{15}$ is hydrogen and $R^{16}$ and $R^{17}$ are independently selected from hydrogen and $C_1$–$C_{10}$ alkyl. The itaconate substrates of formula 14 are generally commercially available or can prepared by methods known to those skilled in the art.

The products of the hydrogenation of itaconates having formula 14 with catalysts based on ligands 1 and 2 are comprised of species with formula 15,

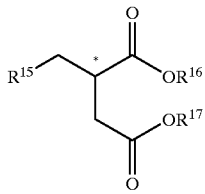

15 wherein $R^{15}$, $R^{16}$, and $R^{17}$ are as defined above. These compounds are generally produced with high enantioselectivity (>80% ee), with the particular enantiomer produced depending upon whether ligand 1 or ligand 2 is used.

The α-ketoester compounds which may be selectively hydrogenated have general formula 16:

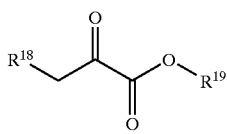

16 wherein $R^{18}$ and $R^{19}$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen; or $R^{18}$ and $R^{19}$ may collectively represent a substituted or unsubstituted alkylene group of 14 chain carbon atoms forming an α-ketolactone.

The α-ketoester substrates of formula 16 are generally commercially available or can prepared by methods known to those skilled in the art.

The preferred α-ketoester reactants have formula 16 wherein $R^{18}$ and $R^{19}$ are independently selected from hydrogen, $C_1$–$C_{10}$ alkyl, $C_3$–$C_6$ cycloalkyl, phenyl, and benzyl. The preferred α-ketoester reactants also include the compounds of formula 16 wherein $R^{18}$ and $R^{19}$ collectively represent a substituted or unsubstituted alkylene group of 2–3 chain carbon atoms forming an α-ketolactone.

The products of the hydrogenation of α-ketoesters having formula 16 with catalysts based on ligands 1 and 2 are comprised of species with formula 17,

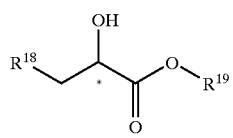

17 wherein $R^{18}$ and $R^{19}$ are as defined above. These compounds are generally produced with high enantioselectivity (>80% ee), with the particular enantiomer produced depending upon whether ligand 1 or ligand 2 is used.

For an asymmetric hydrogenation reaction, the metal complexed can be chosen from the group consisting of rhodium, iridium, or ruthenium, and is most preferably rhodium. The ligand-metal complex can be prepared and isolated, but it is preferable to prepare the complex in situ from ligand 1 or 2 and a metal pre-catalyst. The ligand to metal molar ratio may be in the range of about 0.5:1 to 5:1, preferably about 1:1 to 1.5:1. The amount of complex may vary between 0.00005 and 0.5 equivalents based on the reactant compound, with more complex usually providing faster reaction rates. The atmosphere is hydrogen, but may also contain other materials that are inert to the reaction conditions. The reaction can be run at atmospheric pressure or at elevated pressure, from 0.5–200 bars gauge (barg). The reaction is run at a temperature which affords a reasonable rate of conversion, which can be as low as −50° C. but is usually between ambient temperature and the boiling point (or apparent boiling point at elevated pressure) of the lowest boiling component of the reaction mixture. The reaction is usually run in the presence of a solvent chosen from aliphatic hydrocarbons such as hexane, heptane, octane and the like, aromatic hydrocarbons such as toluene, xylenes, and the like, cyclic or acyclic ethers such as tert-butyl methyl ether, diisopropyl ether, tetrahydrofuran and the like, lower alcohols such as methanol, ethanol, n-propanol, isopropanol, n-butanol and the like, halogenated aliphatic or aromatic hydrocarbons such as dichloromethane, tetrachloroethylene, chloroform, chlorobenzene and the like, dialkyl ketones such as acetone, 2-butanone, 3-pentanone, methyl isopropyl ketone, methyl isobutyl ketone and the like, or polar aprotic solvents such as dimethylformamide, dimethyl sulfoxide and the like.

These reactions are exemplified by the asymmetric hydrogenation reactions of various enamides, itaconates, and α-ketoesters as shown below. The amino-acid derivatives generated from the asymmetric hydrogenation of enamide substrates using a rhodium complex formed in situ from ligands 1 or 2 are generally obtained in very high enantiomeric excess (>90% ee), while the succinate and α-hydroxyester derivatives generated from the asymmetric hydrogenation of, respectively, the itaconate and α-ketoester substrates using a rhodium complex formed in situ from ligands 1 or 2 are generally obtained in high enantiomeric excess (>80% ee).

General Procedure A—Low Pressure Asymmetric Hydrogenation

Bis(1,5-cyclooctadiene)rhodium trifluoromethanesulfonate was placed into a reaction vessel and purged with argon for 15 minutes. A solution of the ligand (1 or 2) in anhydrous tetrahydrofuran (THF, 2.0 mL) was degassed with Ar for 15 minutes, then added via cannula to the bis(1,5-cyclooctadiene)rhodium trifluoromethanesulfonate. This solution was stirred at 25° C. under argon for 15 minutes. A solution of enamide 10 (0.5 mmol) in anhydrous THF (2.0 mL) was degassed with argon for 20 minutes, then added to the catalyst solution via cannula. The solution was then flushed with hydrogen and pressurized to 0.69–1.38 bars gauge (10–20 pounds per square inch gauge—psig) hydrogen. Samples were taken and analyzed for enantiomeric excess using standard analytical techniques (see below).

General Procedure B—High Pressure Asymmetric Hydrogenation

Bis(1,5-cyclooctadiene)rhodium trifluoromethanesulfonate and the ligand (1 or 2) were placed in a high pressure reaction vessel which was sealed and purged with argon. The desired solvent was degassed with Ar for 15 minutes, then 2.0 mL was added to the reaction vessel via syringe. This solution was stirred at 25° C. under argon for 15 minutes. A solution of the desired substrate (0.5 mmol) in the desired degassed solvent (2 mL) was then added to the catalyst solution via syringe. The substrate was washed in with 1 mL of the degassed solvent. The solution was then purged five times with argon and pressurized with hydrogen to the desired pressure (6.9–20.7 barg; 100–300 psig) and heated to the desired temperature. The reactions were run for 6 hours at the desired temperature and pressure, and then cooled (if necessary) to ambient temperature, depressurized, and purged with argon. Samples were taken and analyzed for enantiomeric excess using standard analytical techniques (see below).

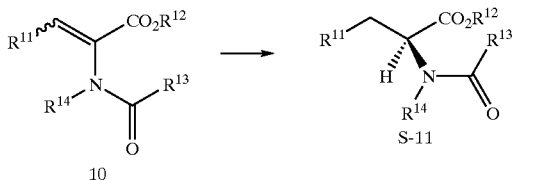

Example 8

N-Acetyl L-phenylalanine Methyl Ester (S-11a)

Enamide 10a ($R^{11}$=phenyl, $R^{12}$=$R^{13}$=methyl, $R^{14}$=H) was hydrogenated according to General Procedure A using bis (1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11a ($R^{11}$=phenyl, $R^{12}$=$R^{13}$=methyl, $R^{14}$=H with 99.2% ee as determined by chiral GC analysis.

$^1$H NMR (CD$_3$OD, 400 MHz) δ 7.28–7.16 (m, 5H); 4.64–4.61 (m, 1H); 3.65 (s, 3H); 3.13–3.08 (dd, 1H, J=5.5, 13.9 Hz); 2.94–2.88 (dd, 1H, J=8.9, 13.9 Hz); 1.87 (s, 3H). Chiral GC [Chirasil L-Valine (Varian) 25 m×0.25 mm ID, film thickness 0.12 μm, 160° C. for 9 min, 160–185° C. at 70° C./min, 185° C. for 5 min, 15 psig He]: $t_R$(R-11a) 7.77 min, $t_R$(S-11a) 8.29 min, $t_R$(10a) 13.24 min.

Example 9

N-Acetyl L-phenylalanine Methyl Ester (S-11a) via High Pressure Hydrogenation in THF Enamide 10a ($R^{11}$=phenyl, $R^{12}$=$R^{13}$=methyl, $R^{14}$=H) was hydrogenated according to General Procedure B in THF using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11a ($R^{11}$=phenyl, $R^{12}$=$R^{13}$=methyl, $R^{14}$=H) with 96.8% ee as determined by chiral GC analysis.

Example 10

N-Acetyl L-phenylalanine methyl ester (S-11a) via High Pressure Hydrogenation in Acetone Enamide 10a ($R^1$=phenyl, $R^{12}$=$R^{13}$=methyl, $R^{14}$=H) was hydrogenated according to General Procedure B in acetone using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11a ($R^{11}$=phenyl, $R^{12}$=$R^{13}$=methyl, $R^{14}$=H) with 97.6% ee as determined by chiral GC analysis.

Example 11

N-Acetyl L-phenylalanine (S-11b)

Enamide 10b ($R^{11}$=phenyl, $R^{12}$=$R^{14}$=H, $R^{13}$=methyl) was hydrogenated according to General Procedure A using bis (1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford 100% conversion to amino acid derivative S-11b ($R^{11}$=phenyl, $R^{12}$=$R^{14}$=H, $R^{13}$=methyl) with 99.4% ee.

A sample was treated with diazomethane to make the methyl ester before analysis. See Example 8 (N-acetyl phenylalanine methyl ester) for analytical details.

$^1$H NMR (CD$_3$OD, 300 MHz) δ 7.20–7.08 (m, 6H); 4.58–4.54 (dd, 1H, J=5.2, 9.1 Hz); 3.14–3.07 (dd, 1H, J=4.9, 13.9 Hz); 2.88–2.80 (dd, 1H, J=9.1, 14.0 Hz); 1.8 (s, 3H).

Example 12

N-t-Butyloxycarbonyl L-phenylalanine methyl ester (S-11c)

Enamide 10c ($R^{11}$=phenyl, $R^{12}$=methyl, $R^{13}$=t-butoxy, $R^{14}$=H) was hydrogenated according to General Procedure A using bis(1,5-cyclooctadiene)rhodium trifluoromethanesulfonate (3.0 mg; 6.5 μmol; 0.013 equiv) and ligand (R,S)-1b (4.4 mg; 7.2 μmol; 0.016 equiv) for 1 hour to afford 100% conversion to amino acid derivative S-11c ($R^{11}$=phenyl, $R^{12}$=methyl, $R^{13}$ t-butoxy, $R^{14}$=H) with 99.5% ee as determined by chiral GC analysis. Chiral GC [Chirasil L-Valine (Varian) 25 m×0.25 mm ID, film thickness 0.12 μm, 140° C. isothermal, 15 psig He]: $t_R$(R-11c) 19.14 min, $t_R$(S-11C) 19.66 min, $t_R$(10c) 40.14 min.

Example 13

N-Benzamido L-phenylalanine methyl ester (S-11d)

Enamide 10d ($R^{11}$=$R^{13}$=phenyl, $R^{12}$=methyl, $R^{14}$=H) was hydrogenated according to General Procedure A using bis (1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11d ($R^{11}=R^{13}$=phenyl, $R^{12}$=methyl, $R^{14}$=H) with 98.4% ee as determined by chiral GC analysis.

$^1$H NMR (CD$_3$OD, 600 MHz) δ 7.72–7.70 (d, 2H, J=7.3 Hz); 7.50–7.47 (m, 1H); 7.40–7.23 (m, 2H); 7.20–7.17 (m, 5H); 4.854.83 (m, 1H); 3.69 (s, 3H); 3.65 (s, 1H); 3.29–3.26 (m, 1H); 3.13–3.08 (m, 1H). Chiral GC [Chirasil L-Valine (Varian) 25 m×0.25 mm ID, film thickness 0.12 μm, 150° C. isothermal, 15 psig He]: $t_R$(R-11d) 11.69 min, $t_R$(S-11d) 12.68 min, $t_R$(10d) 18.5 min.

Example 14

N-Acetyl D-alanine Methyl Ester (R-11e)

Enamide 10e ($R^{11}=R^{14}$=H, $R^{12}=R^{13}$=methyl) was hydrogenated according to General Procedure A using bis(1,5-cyclooctadiene)rhodium trifluoromethanesulfonate (5.8 mg; 12.5 μmol; 0.025 equiv) and ligand (S,R)-2b (9.3 mg; 15 μmol; 0.03 equiv) for 1 hour to afford 100% conversion to amino acid derivative R-11e ($R^{11}=R^{14}$=H, $R^{12}=R^{13}$=methyl) with 98.4% ee as determined by chiral GC analysis.

$^1$H NMR (CD$_3$OD, 600 MHz) δ 4.42–4.38 (dd, 1H, J=7.3,14.7 Hz); 3.72 (s, 3H); 1.98 (s, 3H); 1.38–1.37 (d, 3H, J=7.3 Hz). Chiral GC [Cyclosil-B (J&W Scientific) 30 m×0.25 mm ID, 0.25 um film thickness, 40–100° C. at 70° C./min, 100° C. for 15 min, 100–170° C. at 15° C/min, 170° C. for 7 min, 6 psig He for 6 min, 6–20 psig He at 80 psig/min, 20 psig for 22 min]: $t_R$(R-11e) 19.36 min, $t_R$(S-11e) 19.12 min, $t_R$(10e) 17.91 min.

Example 15

N-Acetyl L-alanine methyl ester (S-11e) via High Pressure Hydrogenation in Acetone Enamide 10e ($R^{11}=R^{14}$=H, $R^{12}=R^{13}$=methyl) was hydrogenated according to General Procedure B in acetone using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford 100% conversion to amino acid derivative R-11e ($R^{11}=R^{14}$=H, $R^{12}=R^{13}$=methyl) with 95.2% ee as determined by chiral GC analysis.

Example 16

N-Acetyl D-alanine (R-11f)

Enamide 10f ($R^{11}=R^{12}=R^{14}$=H, $R^{13}$=methyl) was hydrogenated according to General Procedure A using bis(1,5-cyclooctadiene)rhodium trifluoromethanesulfonate (2.3 mg; 5 μmol; 0.01 equiv) and ligand (S,R)-2b (3.7 mg; 6 μmol; 0.012 equiv) for 24 hours to afford 100% conversion to amino acid derivative R-11f ($R^{11}=R^{12}=R^{14}$=H, $R^{13}$=methyl) with 96.1% ee.

A sample was treated with diazomethane to make the methyl ester before analysis. See Example 14 (N-acetyl alanine methyl ester) for analytical details.

Example 17

N-Benzyloxycarbonyl L-alanine methyl ester (S-11g)

Enamide 10g ($R^{11}=R^{14}$=H, $R^{12}$=methyl, $R^{13}$=benzyloxy) was hydrogenated according to General Procedure A using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford 56% conversion to amino acid derivative S-11g ($R^{11}=R^{14}$=H, $R^{12}$=methyl, $R^{13}$=benzyloxy) with 98.8% ee as determined by chiral GC analysis.

$^1$H NMR (CDCl$_3$, 600MHz) δ 7.33–7.26 (m, 5H); 5.07 (s, 2H); 4.234.19 (m, 1H); 3.69 (s, 3H); 1.36–1.34 (d, 3H, J=7.3 Hz). Chiral GC [Chirasil L-Valine (Varian) 25 m×0.25 mm ID, film thickness 0.12 μm, 150° C. isothermal, 15 psig He]: $t_R$(R-11g) 11.37 min, $t_R$(S-11g) 11.70 min, $t_R$(10g) 10.10 min.

Example 18

N-Benzyloxycarbonyl L-homophenylalanine Ethyl Ester (S-11h)

Enamide 10h ($R^{11}$=benzyl, $R^{12}$=ethyl, $R^{13}$=benzyloxy, $R^{14}$=H) was hydrogenated according to General Procedure A using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) to afford >99% conversion to amino acid derivative S-11h ($R^{11}$=benzyl, $R^{12}$=ethyl, $R^{13}$=benzyloxy, $R^{14}$=H) with 98.1% ee as determined by chiral HPLC analysis.

$^1$H NMR (CDCl$_3$, 400 MHz) δ 7.37–7.15 (m, 10H); 5.38–5.36 (d, 1H, J=7.9 Hz); 5.12 (s, 2H); 4.444.39 (dd, 1H, J=7.6, 13.0 Hz); 4.20–4.15 (dd, 2H, J=7.0, 14.3 Hz); 2.73–2.60 (m, 2H); 2.27–2.14 (m, 1H); 2.02–1.93 (m, 1H); 1.28–1.25 (t, 3H, J=7.0 Hz). A chiral normal-phase HPLC separation of the two enantiomers was developed using a Cyclobond I 2000 SN column (Advanced Separation Technologies, Inc.). Ultraviolet detection was used at a wavelength of 210 nm. The mobile phase was 9713 heptane/isopropanol (v/v). $t_R$(R-11h) 28.93 min, $t_R$(S-11h) 30.99 min, $t_R$(10h) 33.39 min.

Example 19

N-Acetyl L-4-chlorophenylalanine Methyl Ester (S-11i)

Enamide 10i ($R^{11}$=4-chlorophenyl, $R^{12}=R^{13}$=methyl, $R^{14}$=H) was hydrogenated according to General Procedure A using bis(1,5-cyclooctadiene)rhodium trifluoromethanesulfonate (4.6 mg; 10 μmol; 0.02 equiv) and ligand (R,S)-11b (7.4 mg; 12 μmol; 0.024 equiv) for 2 hours to afford 100% conversion to amino acid derivative S-11i ($R^{11}$=4-chlorophenyl, $R^{12}=R^{13}$=methyl, $R^{14}$=H) with 98.8% ee as determined by chiral GC analysis.

$^1$H NMR (CD$_3$OD, 600 MHz) 7.27–7.25 (d, 2H, J=8.7 Hz); 7.18–7.16 (d, 2H, J=8.7 Hz); 4.644.62 (dd, 1H, J=5.5, 9.2 Hz); 3.70 (s, 1H); 3.67 (s, 3H), 3.13–3.09 (dd, 1H, J=5.5,13.7 Hz); 2.93–2.89 (dd, 1H, J=9.2, 13.9 Hz); 1.88 (s, 3H). Chiral GC [Chirasil L-Valine (Varian) 25 m×0.25 mm ID, film thickness 0.12 μm, 175° C. isothermal, 20 psig He]: $t_R$(R-11i) 7.29 min, $t_R$(S-11i) 7.76 min, $t_R$(10i) 15.72 min.

Example 20

N-Acetyl L-4-chlorophenylalanine methyl ester (S-11i) via High Pressure Hydrogenation in THF Enamide 10i ($R^{11}$=4-chlorophenyl, $R^{12}=R^{13}$=methyl, $R^{14}$=H) was hydrogenated according to General Procedure B in THF using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11i ($R^{11}$=4-chlorophenyl, $R^{12}=R^{13}$=methyl, $R^{14}$=H) with 96.2% ee as determined by chiral GC analysis.

Example 21

N-Acetyl L-4-cyanophenylalanine methyl ester (S-11j)

Enamide 10j ($R^{11}$=4-cyanophenyl, $R^{12}$=$R^{13}$=methyl, $R^{14}$=H) was hydrogenated according to General Procedure A using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford 100% conversion to amino acid derivative S-11j ($R^{11}$=4-cyanophenyl, $R^{12}$=$R^{13}$=methyl, $R^{14}$=H) with 99.0% ee as determined by chiral GC analysis. Chiral GC [Chirasil L-Valine (Varian) 25 m×0.25 mm ID, film thickness 0.12 μm, 190° C. isothermal, 20 psig He]: $t_R$(R-11j) 8.73 min, $t_R$(S-11j) 9.17 min.

Example 22

N-Acetyl L-4-methoxyphenylalanine methyl ester (S-11k)

Enamide 10k ($R^{11}$=4-methoxyphenyl, $R^{12}$=$R^{13}$=methyl, $R^{14}$=H) was hydrogenated according to General Procedure A using bis(1,5-cyclooctadiene)rhodium trifluoromethanesulfonate (4.6 mg; 10 μmol; 0.02 equiv) and ligand (R,S)-1b (7.4 mg; 12 μmol; 0.024 equiv) for 30 minutes to afford 90% conversion to amino acid derivative S-11k ($R^{11}$=4-methoxyphenyl, $R^{12}$=$R^{13}$=methyl, $R^{14}$=H) with 97.9% ee as determined by chiral GC analysis.

$^1$H NMR (CD$_3$OD, 400 MHz) δ 7.09–7.07 (d, 2H, J=8.9 Hz); 6.82–6.80 (d, 2H, J=8.9 Hz); 4.59–4.56 (dd, 1H J=5.8, 8.9 Hz); 3.73 (s, 3H); 3.70 (s, 1H); 3.65 (s, 3H); 3.06–3.01 (dd, 1H, J=5.8, 13.7 Hz); 2.88–2.82 (dd, 1H, J=8.9, 13.9 Hz); 1.88 (s, 3H). Chiral GC [Chirasil L-Valine (Varian) 25 m×0.25 mm ID, film thickness 0.12 μm, 1850C isothermal, 20 psig He]: $t_R$(R-11k) 6.04 min, $t_R$(S-11k) 6.32 min, $t_R$(10k) 15.13 min.

Example 23

N-Acetyl L-4-methoxyphenylalanine Methyl Ester (S-11k) via High Pressure Hydrogenation in THF Enamide 10k ($R^{11}$=4-methoxyphenyl, $R^{12}$=$R^{13}$=methyl, $R^{14}$=H) was hydrogenated according to General Procedure B in THF using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11k ($R^{11}$=4-methoxyphenyl, $R^{12}$=$R^{13}$=methyl, $R^{14}$=H) with 97.3% ee as determined by chiral GC analysis.

Example 24

N-Acetyl L-3-methoxyphenylalanine Methyl Ester (S-11m)

Enamide 10m ($R^{11}$=3-methoxyphenyl, $R^{12}$=$R^{13}$=methyl, $R^{14}$=H) was hydrogenated according to General Procedure A using bis(1,5-cyclooctadiene)rhodium trifluoromethanesulfonate (4.6 mg; 10 μmol; 0.02 equiv) and ligand (R,S)-1b (7.4 mg; 12 μmol; 0.024 equiv) for 30 minutes to afford 100% conversion to amino acid derivative S-11m ($R^{11}$=3-methoxyphenyl, $R^{12}$=$R^{13}$=methyl, $R^{14}$=H) with 98.0% ee as determined by chiral GC analysis.

$^1$H NMR (CD$_3$OD, 400 MHz) δ 7.19–7.15 (t, 1H, J=7.9 Hz,); 6.78–6.74 (m, 3H); 4.66–4.62 (dd, 1H, J=5.5, 9.0 Hz); 3.75 (s, 3H); 3.72–3.69 (m, 1H); 3.67 (s, 3H); 3.12–3.07 (dd, 1H, J=5.8, 13.9 Hz); 2.92–2.88 (dd, 1H, J=8.9,13.7 Hz); 1.89 (s, 3H). Chiral GC [Chirasil L-Valine (Varian) 25 m×0.25 mm ID, film thickness 0.12 μm, 185° C. isothermal, 20 psig He]: $t_R$(R-11m) 7.73 min, $t_R$(S-11m) 8.18 min.

Example 25

N-Acetyl L-2-methoxyphenylalanine methyl ester (S-11n)

Enamide 10n ($R^{11}$=2-methoxyphenyl, $R^{12}$=$R^{13}$=methyl, $R^{14}$=H) was hydrogenated according to General Procedure A using bis(1,5-cyclooctadiene)rhodium trifluoromethanesulfonate (4.6 mg; 10 μmol; 0.02 equiv) and ligand (R,S)-1b (7.4 mg; 12 μmol; 0.024 equiv) for 2 hours to afford 99.5% conversion to amino acid derivative S-11n (R=2-methoxyphenyl, $R^{12}$=$R^{13}$=methyl, $R^{14}$=H) with 97.7% ee as determined by chiral GC analysis.

$^1$H NMR (CD$_3$OD, 600 MHz) δ 7.21–7.19 (t, 1H, J=7.3 Hz); 7.06–7.05 (d, 1H, J=7.3 Hz); 6.92–6.90 (d, 1H, J=7.8 Hz); 6.84–6.82 (t, 1H, J=7.8 Hz); 4.67–4.66 (m, 1H); 3.82 (s, 3H); 3.70 (s, 1H); 3.63 (s, 3H); 3.16–3.13 (dd, 1H, J=6.0, 13.5 Hz); 2.90–2.86 (dd, 1H, J=8.7,13.3 Hz); 1.86 (s, 3H). Chiral GC [Chirasil L-Valine (Varian) 25 m×0.25 mm ID, film thickness 0.12 μm, 185° C. isothermal, 20 psig He]: $t_R$(R-11n) 4.87 min, $t_R$(S-11n) 5.07 min, $t_R$(10n) 8.96 min.

Example 26

N-Acetyl L-2-methoxyphenylalanine methyl ester (S-11n) via High Pressure Hydrogenation in THF Enamide 10n ($R^{11}$=2-methoxyphenyl, $R^{12}$=$R^{13}$=methyl, $R^{14}$=H) was hydrogenated according to General Procedure B in THF using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 100% conversion to amino acid derivative S-11n ($R^{11}$=2-methoxyphenyl, $R^{12}$=$R^{13}$=methyl, $R^{14}$=H) with 96.7% ee as determined by chiral GC analysis.

Example 27

N-Acetyl L-4-nitrophenylalanine Methyl Ester (S-10)

Enamide 10o ($R^{11}$=4-nitrophenyl, $R^{12}$=$R^{13}$=methyl, $R^{14}$=H) was hydrogenated according to General Procedure A using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 30 minutes to afford 100% conversion to amino acid derivative S-11o ($R^{11}$=4-nitrophenyl, $R^{12}$=$R^{13}$=methyl, $R^{14}$=H) with 97.7% ee as determined by chiral GC analysis.

$^1$H NMR (CD$_3$OD, 400 MHz) δ 8.15–8.13 (d, 2H, J=8.9 Hz,); 7.45–7.43 (d, 2,H J=8.6 Hz); 4.75–4.71 (dd, 1H, J=5.5, 9.2 Hz,); 3.69 (s, 3H); 3.67 (s, 1H); 3.30–3.25 (m, 1H); 3.08–3.02 (m, 1H); 1.88 (s, 3H). Chiral GC [Chirasil L-Valine (Varian) 25 m×0.25 mm ID, film thickness 0.12 μm, 185° C. isothermal, 20 psig He]: $t_R$(R-11o) 15.73 min, $t_R$(S-11o) 16.79 min.

Example 28

N-t-Butyloxycarbonyl L-3-furanylalanine Methyl Ester (S-11p)

Enamide 10p ($R^{11}$=3-furanyl, $R^{12}$=methyl, $R^{13}$=t-butoxy, $R^{14}$=H) was hydrogenated according to General Procedure A using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 98% conversion to amino acid derivative S-11p ($R^{11}$=3-furanyl, $R^{12}$=methyl, $R^{13}$=t-butoxy, $R^{14}$=H) with 97.2% ee as determined by chiral GC analysis.

$^1$H NMR (CDCl$_3$, 300 MHz) δ 7.36 (s, 1H); 7.25 (s, 1H); 6.21 (s, 1H); 5.12–5.09 (m, 1H); 4.53–4.51 (m, 1H); 3.73 (s, 3H); 2.93–2.92 (m, 2H); 1.44 (s, 9H). Chiral GC [Chirasil L-Valine (Varian) 25 m×0.25 mm ID, film thickness 0.12 μm, 140° C. isothermal, 20 psig He]: $t_R$(R-11p) 7.61 min, $t_R$(S-11p) 7.89 min, $t_R$(10P) 17.97 min.

Example 29

N-Benzamido D-3-furanylalanine Methyl Ester (R-11q)

Enamide 10q ($R^{11}$=3-furanyl, $R^{12}$=methyl, $R^{13}$=phenyl, $R^{14}$=H) was hydrogenated according to General Procedure A using bis(1,5-cyclooctadiene)rhodium trifluoromethanesulfonate (2.3 mg; 5 μmol; 0.01 equiv) and ligand (S,R)-2b (3.7 mg; 6 μmol; 0.012 equiv) for 6 hours to afford 100% conversion to amino acid derivative R-11q ($R^{11}$=3-furanyl, $R^{12}$=methyl, $R^{13}$=phenyl, $R^{14}$=H) with 96.6% ee as determined by chiral GC analysis.

$^1$H NMR (CD$_3$OD, 400 MHz) δ 7.77–7.75 (m, 2H); 7.53–7.36 (m, 6H); 4.79–4.75 (dd, 1H, J=5.2, 9.3 Hz); 3.72 (s, 3H); 3.69 (s, 1H); 3.11–3.06 (dd, 1H, J=5.2, 14.6 Hz); 2.99–2.93 (dd, 1H, J=9.5,14.6 Hz). Chiral GC [Chirasil L-Valine (Varian) 25 m×0.25 mm ID, film thickness 0.12 μm, 175° C. isothermal, 20 psig He]: $t_R$(R-11q) 12.57 min, $t_R$(S-11q) 13.29 min, $t_R$(10q) 9.39 min.

Example 30

N-t-Butyloxycarbonyl L-cyclopropylalanine methyl ester (S-11r)

Enamide 10r ($R^{11}$=cyclopropyl, $R^{12}$=methyl, $R^{13}$=t-butoxy, $R^{14}$=H) was hydrogenated according to General Procedure A using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 90% conversion to amino acid derivative S-11r ($R^{11}$=cyclopropyl, $R^{12}$=methyl, $R^{13}$=t-butoxy, $R^{14}$=H) with 98.6% ee as determined by chiral GC analysis.

$^1$H NMR (CDCl$_3$, 300 MHz) δ 5.22–5.20 (m, 1H); 4.41–4.34 (m, 1H); 3.74 (s, 3H); 1.69–1.64 (t, 2H, J=6.6 Hz); 0.73–0.67 (m, 1H); 0.51–0.44 (m, 2H); 0.10–0.05 (m, 2H). Chiral GC [Chirasil L-Valine (Varian) 25 m×0.25 mm ID, film thickness 0.12 μm, 175° C. isothermal, 15 psig He]: $t_R$(R-11r) 14.59 min, $t_R$(S-11r) 15.21 min, $t_R$(10r) 26.34 min.

Example 31

N-Benzamido D-cyclopropylalanine Methyl Ester (R-11s)

Enamide 10s ($R^{11}$=cyclopropyl, $R^{12}$=methyl, $R^{13}$=phenyl, $R^{14}$=H) was hydrogenated according to General Procedure A using bis(1,5-cyclooctadiene)rhodium trifluoromethanesulfonate (2.3 mg; 5 μmol; 0.01 equiv) and ligand (S,R)-2b (3.7 mg; 6 μmol; 0.012 equiv) for 24 hours to afford 100% conversion to amino acid derivative R-1 1s ($R^{11}$=cyclopropyl, $R^{12}$=methyl, $R^{13}$=phenyl, $R^{14}$=H) with 91.6% ee as determined by chiral GC analysis.

$^1$H NMR (CDCl$_3$, 300 MHz) δ 7.80–7.76 (m, 2H); 7.50–7.36 (m, 3H); 4.62–4.57 (m, 1H); 3.66 (s, 3H); 1.81–1.75 (m, 1H); 1.69–1.63 (m, 1H); 0.80–0.75 (m, 1H); 0.45–0.39 (m, 2H); 0.09–0.04 (m, 2H). $^{13}$C NMR (CDCl$_3$, 75 MHz) δ 133.0, 129.7, 128.7, 55.3, 52.9, 37.5, 23.6, 9.1, 5.4, 4.8. Chiral GC [Chirasil L-Valine (Varian) 25 m×0.25 mm ID, film thickness 0.12 μm, 175° C. isothermal, 20 psig He]: $t_R$(R-11s) 10.76 min, $t_R$(S-11s) 11.18 min, $t_R$(10S) 17.73 min.

Example 32

N-t-Butyloxycarbonyl L-cyclopropylalanine Benzyl Ester (S-11t)

Enamide 10t ($R^{11}$=cyclopropyl, $R^{12}$=benzyl, $R^{13}$=t-butoxy, $R^{14}$=H) was hydrogenated according to General Procedure A in acetone as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford 94% conversion to amino acid derivative S-11 t ($R^{11}$=cyclopropyl, $R^{12}$=benzyl, $R^{13}$=t-butoxy, $R^{14}$=H) with >99% ee as determined by chiral GC analysis.

$^1$H NMR (CDCl$_3$, 300MHz) δ 7.414.30 (m, 5H); 5.13–5.12 (m, 1H); 5.02 (s, 2H); 1.70–1.60 (m, 2H); 1.45 (s, 9H); 0.69–0.61 (m, 1H); 0.42–0.39 (m, 2H); 0.02–0.01 (m, 2H). Chiral GC [Chirasil L-Valine (Varian) 25 m×0.25 mm ID, film thickness 0.12 μm, 175° C. isothermal, 15 psig He]: $t_R$(R-11t) 15.03 min, $t_R$(S-11t) 15.48 min, $t_R$(10t) 25.98 min.

Example 33

N-t-Butyloxycarbonyl L-cyclopropylalanine Benzyl Ester (S-11t) via High Pressure Hydrogenation in Acetone Enamide 10t ($R^{11}$=cyclopropyl, $R^{12}$=benzyl, $R^{13}$=t-butoxy, $R^{14}$=H) was hydrogenated according to General Procedure B in acetone as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford 100% conversion to amino acid derivative S-11t ($R^{11}$=cyclopropyl, $R^{12}$=benzyl, $R^{13}$=t-butoxy, $R^{14}$=H) with 95.5% ee as determined by chiral GC analysis.

Example 34

N-Acetyl 1-Naphthylalanine methyl ester (S-11u)

Enamide 10u ($R^{11}$=1-naphthyl, $R^{12}$=$R^{13}$=methyl, $R^{14}$=H) was hydrogenated according to General Procedure A in THF as solvent using bis(1,5-cyclooctadiene)rhodium trifluoromethanesulfonate (2.3 mg; 5 μmol; 0.01 equiv) and ligand (R,S)-1 b (3.7 mg; 6 μmol; 0.012 equiv) for 6 hours to afford >95% conversion to amino acid derivative S-11u ($R^{11}$=1-naphthyl, $R^{12}$=$R^{13}$=methyl, $R^{14}$=H) with 99.3% ee as determined by chiral GC analysis.

$^1$H NMR (CDCl$_3$, 300 MHz) δ 8.083 (d, 1H, J=8.24 Hz); 7.855 (d, 1H, J=7.69 Hz); 7.769 (d, 1H, J=7.97 Hz); 7.510 (m(5), 2H, J=7.97 Hz); 7.385 (t, 1H, J=7.14 Hz); 7.230 (d, 1H, J=6.87 Hz); 5.98 (br s, 1H); 5.017 (q, 1H, J=6.59 Hz); 3.626 (s, 3H); 3.57 (m, 2H); 1.926 (s, 3H). Chiral GC [Chirasil L-Valine (Varian) 25 m×0.25 mm ID, film thickness 0.12 μm, 185° C. for 22 min, 185–195° C. at 1°° C/min, 195° C. for 17 min, 15 psig He]: $t_R$(R-11u) 18.83 min, $t_R$(S-11U) 19.76 min.

Example 35

N-Acetyl 1-Naphthylalanine Methyl Ester (S-11u) via High Pressure Hydrogenation

Enamide 10u ($R^{11}$=1-naphthyl, $R^{12}$=$R^{13}$=methyl, $R^{14}$=H) was hydrogenated according to General Procedure B in acetone as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford >95% conversion to amino acid derivative S-11u ($R^{11}$=1-naphthyl, $R^{12}$=$R^{13}$=methyl, $R^{14}$=H) with 97.4% ee as determined by chiral GC analysis.

Example 36

N-t-Butyloxycarbonyl 1-Naphthylalanine methyl ester (S-11v)

Enamide 10v ($R^{11}$=1-naphthyl, $R^{12}$=methyl, $R^{13}$=t-butoxy, $R^{14}$=H) was hydrogenated according to General Procedure A in THF as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford >95% conversion to amino acid derivative S-11v ($R^{11}$=1-naphthyl, $R^{12}$=methyl, $R^{13}$=t-butoxy, $R^{14}$=H) with 98.2% ee as determined by chiral HPLC analysis.

$^1$H NMR (CDCl$_3$, 300 MHz) δ 8.075 (d, 1H, J=7.96 Hz); 7.858 (d, 1H, J=7.69 Hz); 7.767 (d, 1H, J=8.24 Hz); 7.512 (m(5), 2H, J=7.97 Hz); 7.391 (t, 1H, J=7.14 Hz); 7.27 (m, 1H); 5.057 (br d, 1H, J=7.69 Hz); 4.719 (q, 1H, J=7.69 Hz); 3.744 (s, 3H); 3.7–3.4 (m, 2H); 1.395 (s, 9H). Chiral HPLC [Chiralcel OD-H (Diacel Chemical), 250×4.6 mm, 95:5 hexane:isopropanol, 1 mL/min, λ=254 nm]: $t_R$(R-11v) 14.05 min, $t_R$(S-11V) 17.64 min.

Example 37

N-Acetyl 2-Naphthylalanine methyl ester (S-11w)

Enamide 10w ($R^{11}$=2-naphthyl, $R^{12}$=$R^{13}$=methyl, $R^{14}$=H) was hydrogenated according to General Procedure A in THF as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 1 hour to afford >95% conversion to amino acid derivative S-11w ($R^{11}$=2-naphthyl, $R^{12}$=$R^{13}$=methyl, $R^{14}$=H) with 98.1% ee as determined by chiral GC analysis.

$^1$H NMR (CDCl$_3$, 300 MHz) δ 7.85–7.75 (m, 3H); 7.553 (s, 1H); 7.47 (m, 2H); 7.218 (d, 1H, J=8.52 Hz); 6.01 (br s, 1H); 4.966 (q, 1H, J=6.04 Hz); 3.727 (s, 3H); 3.314 (dd, 1H, J=5.77, 13,74 Hz); 3.244 (dd, 1H, J=6.04, 14.01 Hz); 1.973 (s, 3H). Chiral GC [Chirasil L-Valine (Varian) 25 m×0.25 mm ID, film thickness 0.12 μm, 185° C. isothermal, 15 psig He]: $t_R$(R-11w) 22.02 min, $t_R$(S-11w) 23.26 min.

Example 38

N-Acetyl 2-Naphthylalanine Methyl Ester (S-11w) via High Pressure Hydrogenation

Enamide 10w ($R^{11}$=2-naphthyl, $R^{12}$=$R^{13}$=methyl, $R^{14}$=H) was hydrogenated according to General Procedure B in acetone as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford >95% conversion to amino acid derivative S-11w ($R^{11}$=2-naphthyl, $R^{12}$=$R^{13}$=methyl, $R^{14}$=H) with 97.6% ee as determined by chiral GC analysis.

Example 39

N-t-Butyloxycarbonyl 2-Naphthylalanine Methyl Ester (S-11x)

Enamide 10x ($R^{11}$=2-naphthyl, $R^{12}$=methyl, $R^{13}$=t-butoxy, $R^{14}$=H) was hydrogenated according to General Procedure A in THF as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 97% conversion to amino acid derivative S-11x ($R^{11}$=2-naphthyl, $R^{12}$=methyl, $R^{13}$=t-butoxy, $R^{14}$=H) with 97.4% ee as determined by chiral HPLC analysis. $^1$H NMR (CDCl$_3$, 300 MHz) δ 7.80 (m, 3H); 7.586 (s, 1H,); 7.45 (m, 2H); 7.26 (m, 1H); 5.000 (br d, 1H, J=7.14 Hz); 4.677 (q, 1H, J=6.87 Hz); 3.713 (s, 3H); 3.35–3.15 (m, 2H); 1.399 (s, 9H). Chiral HPLC [Chiralcel OD-H (Diacel Chemical), 250×4.6 mm, 95:5 hexane:isopropanol, 1 mL/min, λ=254 nm]: $t_R$(R-11x) 12.86 min, $t_R$(S-11x) 14.41 min.

Example 40

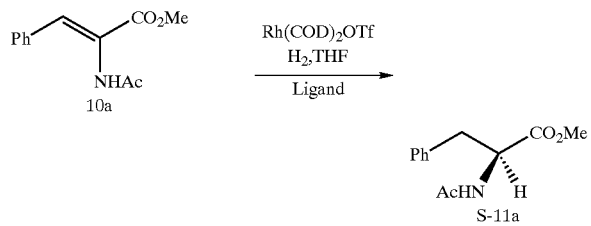

Enamide 10a was hydrogenated according to General Procedure A for 1 hour using bis(1,5-cyclooctadiene) rhodium trifluoromethanesulfonate (2.3 mg; 5 μmol; 0.01 equiv) and the ligands indicated below (6 μmol; 0.012 equiv) to afford in all cases 100% conversion to amino acid derivative 11a with the indicated enantiomeric purity as determined by chiral GC analysis (see Example 8 for analytical details).

| Ligand | 11a Configuration | 11a ee (%) |
|---|---|---|
| (R,S)-1a | S | 97.2 |
| (R,S)-1b | S | 99.1 |
| (R,S)-1c | S | 94.3 |
| (S,R)-2d | R | 93.3 |

Example 41

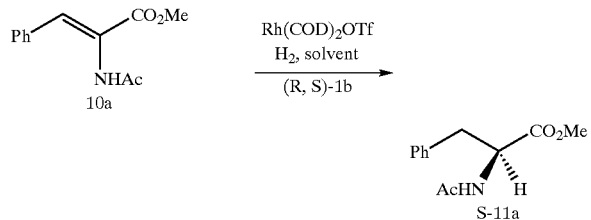

Enamide 10a was hydrogenated according to General Procedure A for 1 hour using bis(1,5-cyclooctadiene) rhodium trifluoromethanesulfonate and ligand (R,S)-1b in the indicated solvent to afford amino acid derivative S-11a with the conversion and enantiomeric excess indicated (see Example 8 for analytical details).

| Solvent | % ee | % conv. | Solvent | % ee | % conv. |
|---|---|---|---|---|---|
| THF | 99.1 | 100 | EtOAc | 98.5 | 100 |
| MeOH | 98.5 | 100 | TBME | >99 | 2% |
| iPrOH | 97.7 | 100 | DMF | 96.5 | 25 |
| Acetone | 98.3 | 97 | DMSO | 94.4 | 15 |
| PhMe | 97.4 | 100 | $CH_2Cl_2$ | 97.9 | 99 |

Tetrahydrofuran (THF), toluene (PhMe), t-butyl methyl ether (TBME), and methanol (MeOH) were anhydrous and used as received. Dichloromethane ($CH_2Cl_2$), acetone, 2-propanol (iPrOH), ethyl acetate (EtOAc), N,N-dimethylformamide (DMF), and dimethyl sulfoxide (DMSO) were not strictly anhydrous nor dried prior to use.

Example 42

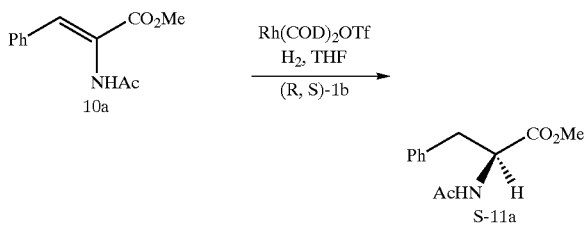

(R,S)-1b was placed in an uncapped vial and left exposed to ambient conditions (25° C.) for seven months prior to use. Bis(1,5-cyclooctadiene)rhodium trifluoromethanesulfonate (2.3 mg; 5 µmol, 0.01 equiv) was placed into a reaction vessel and purged with argon for 15 minutes. A solution of (R,S)-1b (3.7 mg; 6 µmol, 0.012 equiv) in anhydrous THF (2.0 mL) was degassed with argon for 15 minutes, then added via cannula to the bis(1,5-cyclooctadiene)rhodium trifluoromethanesulfonate. This solution was stirred at 25° C. under argon for 15 minutes. A solution of enamide 10a (0.5 mmol) in anhydrous THF (2.0 mL) was degassed with argon for 20 minutes, then added to the catalyst solution via cannula. The solution was then flushed with hydrogen and pressurized to 0.69–1.38 barg (10–20 psig) hydrogen. The reaction was depressurized after 1 hour. N-acetyl L-phenylalanine methyl ester (S-11a) was isolated in 100% yield and 98.8% ee (see Example 8 for analytical details).

Example 43

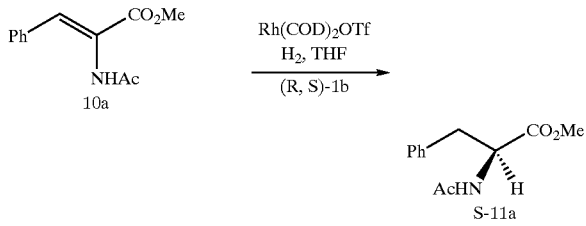

Enamide 10a (5.48 g; 25.0 mmol) was added to a dry nitrogen-purged Fisher-Porter bottle. Argon-degassed methanol (32 mL) was added to afford a homogeneous solution which was purged with argon for 10 minutes. The bottle was fitted with a pressure head and evacuated and filled with argon ten times. To a dry 25-mL flask was added bis(1,5-cyclooctadiene)rhodium trifluoromethanesulfonate (1.2 mg; 0.0025 mmol; 0.0001 equiv) and ligand (R,S)-1b (1.7 mg, 0.0028 mmol; 0.00011 equiv) which had been open to the air at ambient temperature for more than seven months. The flask was purged with argon and 2 mL of argon-degassed THF was added to afford a homogeneous solution. This was allowed to stand for 15 min and then added via a gas-tight syringe to the Fisher-Porter bottle containing the methanolic solution of 10a. The bottle was evacuated and filled with argon ten times, and then evacuated and filled with hydrogen 5 times. The bottle was pressurized with 45 psig hydrogen, sealed, and stirred vigorously at ambient temperature. Hydrogen uptake was immediate and rapid, and was essentially complete after 70 minutes. The reaction mixture was evacuated and filled with argon five times and then depressurized. The reaction mixture was sampled and analyzed by chiral GC to indicate 96.3% conversion to S-11a with 96.8% ee. The reaction mixture was evaporated to afford 5.27 g (95%) of product. See Example 8 for analytical details.

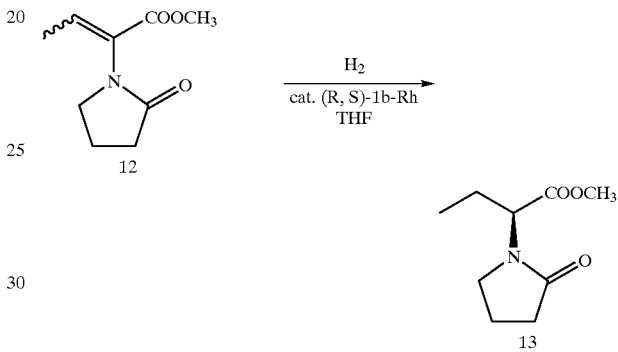

Example 44

Hydrogenation of Enamide 12 to Produce Ester 13 Using Ligand (R,S)-1b

A Fischer-Porter tube was charged with ligand (R,S)-1b (22 mg, 0.036 mmol; 0.064 equivalents) and anhydrous THF (4.0 mL) under an argon atmosphere. Argon was bubbled through the solution for 20 minutes before the addition of bis(1,5-cyclooctadiene)rhodium trifluoromethanesulfonate (12 mg; 0.026 mmol; 0.047 equivalents). The solution was stirred at 25° C. for 5 minutes or until all of the bis(1,5-cyclooctadiene)rhodium trifluoromethanesulfonate had dissolved. Enamide 12(100 mg, 0.55 mmol) was added via syringe. The vessel was capped and pressurized to 2.75 barg (40 psig) hydrogen. After 18 hours, the mixture was diluted with hexane (4.0 mL) and filtered through silica gel to remove the catalyst. The product 13 was isolated as an oil (99% yield, 96.2% ee as determined by chiral GC).

$^1$H NMR (CDCl$_3$) δ 4.714.65 (m, 1H); 3.71 (s, 3H); 3.55–3.47 (m, 1H); 3.38–3.30 (m, 1H); 2.45–2.40 (t, 2H, J=8.4 Hz); 2.12–1.97 (m, 3H); 1.74–1.64 (m, 1H); 0.94–0.89 (t, 3H, J=7.5 Hz). Chiral GC [Cyclosil-B (J&W Scientific), 40° C. for 4 min, 40° C. to 175° C. at 70° C./min, hold at 175° C. for 12 minutes]: t$_R$=23.19 (major enantiomer), t$_R$=23.24 (minor enantiomer).

Example 45

Hydrogenation of Enamide 12 to Produce Ester 13 Using Ligand (S, R)-2a

This hydrogenation was carried out as in the previous example except that ligand (S,R)-2a was used instead of (R,S)-1b. This afforded the product 13 in 90.8% ee.

Example 46

Hydrogenation of Enamide 12 to Produce Ester 13 Using Ligand (R,S)-1b via High Pressure Hydrogenation in THF Enamide 12 was hydrogenated according to General Procedure B in THF as solvent using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 94.9% conversion to amino acid derivative 13 with 92.8% ee as determined by chiral GC analysis.

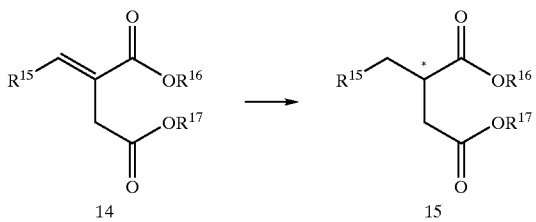

Example 47

Dimethyl Methylsuccinate (15a, $R^{15}$=H, $R^{16}$=$R^{17}$=Me) using Ligand (R,S)-1a in THF at Low Pressure Dimethyl itaconate (14a, $R^{15}$=H, $R^{16}$=$R^{17}$=Me) was hydrogenated according to General Procedure A in THF at 0.69–1.38 bars gauge (10–20 psig) hydrogen at ambient temperature using bis(1,5-cyclooctadiene)rhodium trifluoromethanesulfonate (2.3 mg; 5 μmol; 0.01 equiv) and ligand (R,S)-1a (3.6 mg; 6 μmol; 0.012 equiv) for 6 hours to afford 95% conversion to dimethyl methylsuccinate(15a, $R^{15}$=H, $R^{16}$=$R^{17}$=Me) with 80.2% ee as determined by chiral GC analysis. The analytical properties of 15a were identical to an authentic sample. Chiral GC [Cyclosil-B (J&W Scientific) 30 m×0.25 mm ID, film thickness 0.25 μm, 90° C. isothermal, 15 psig He]: $t_R$(enantiomer 1, 15a) 17.36 min, $t_R$(enantiomer 2, 15a) 17.82 min, $t_R$(14a) 23.16 min.

Example 48

Dimethyl Methylsuccinate (15a, $R^{15}$=H, $R^{16}$=$R^{17}$=Me) using Ligand (R,S)-1a in Acetone at High Pressure Dimethyl itaconate (14a, $R^{15}$=H, $R^{16}$=$R^7$=Me) was hydrogenated according to General Procedure B in acetone at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1a (3.6 mg; 6 μmol; 0.012 equiv) for 6 hours to afford 100% conversion to dimethyl methylsuccinate(15a, $R^{15}$=H, $R^{16}$=$R^{17}$=Me) with 89.1% ee as determined by chiral GC analysis.

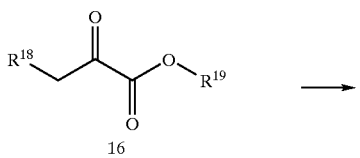

-continued

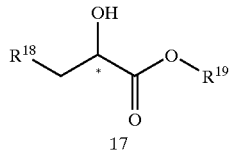

Example 49

Methyl Lactate (17a, $R^{18}$=H, $R^{19}$=Me) using Ligand (R,S)-1b in THF at Low Pressure Methyl pyruvate (16a, $R^{18}$=H, $R^{19}$=methyl) was hydrogenated according to General Procedure A in THF at 0.69–1.38 bars gauge (10–20 psig) hydrogen at ambient temperature using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 8 hours to afford 90.2% conversion to methyl R-lactate (R-17a, $R^{18}$=H, $R^{19}$=methyl) with 88.2% ee as determined by chiral GC analysis. The analytical properties of 17a were identical to an authentic sample. Chiral GC [Cyclosil-B (J&W Scientific) 30 m×0.25 mm ID, film thickness 0.25 μm, 75° C. isothermal, 15 psig He]: $t_R$(R-17a) 7.75 min, $t_R$(S-17a) 9.16 min, $t_R$(16a) 5.16 min.

Example 50

Methyl Lactate (17a, $R^{18}$=H, $R^{19}$=Me) using Ligand (R,S)-1b in THF at High Pressure Methyl pyruvate (16a, $R^{18}$=H, $R^{19}$=methyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 8 hours to afford 98.3% conversion to methyl R-lactate (R-17a, $R^{18}$=H, $R^{19}$=methyl) with 86.8% ee as determined by chiral GC analysis.

Example 51

Methyl Lactate (17a, $R^{18}$=H, $R^{19}$=Me) using Ligand (R,S)-1b in Toluene at High Pressure Methyl pyruvate (16a, $R^{18}$=H, $R^{19}$=methyl) was hydrogenated according to General Procedure B in toluene at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford >95% conversion to methyl R-lactate (R-17a, $R^{18}$=H, $R^{19}$=methyl) with 83.2% ee as determined by chiral GC analysis.

Example 52

Methyl Lactate (17a, $R^{18}$=H, $R^{19}$=Me) using Ligand (R,S)-1d in THF at Low Pressure Methyl pyruvate (16a, $R^{17}$=H, $R^{18}$=methyl) was hydrogenated at ambient temperature according to General Procedure A in THF at 0.69–1.38 bars gauge (10–20 psig) hydrogen using bis(1,5-cyclooctadiene)rhodium trifluoromethanesulfonate (2.3 mg; 5 μmol; 0.01 equiv) and ligand (R,S)-1d (3.8 mg; 6 μmol; 0.012 equiv) for 1 hour to afford 21.1% conversion to methyl R-lactate (R-17a, $R^{18}$=H, $R^{19}$=methyl) with 87.4% ee as determined by chiral GC analysis.

Example 53

Methyl Lactate (17a, $R^{18}$=H, $R^{19}$=Me) using Ligand (R,S)-1d in THF at High Pressure Methyl pyruvate (16a, $R^{18}$=H, $R^{19}$=methyl) was hydrogenated at ambient temperature according to General Procedure B in THF at 20.7 barg (300 psig) hydrogen using bis(1,5-cyclooctadiene)rhodium trifluoromethanesulfonate (2.3 mg; 5 μmol; 0.01 equiv) and ligand (R,S)-1d (3.8 mg; 6 μmol; 0.012 equiv) for 6 hours to afford 98.8% conversion to methyl R-lactate (R-17a, $R^{18}$=H, $R^{19}$=methyl) with 83.8% ee as determined by chiral GC analysis.

Example 54

Methyl Lactate (17a, $R^{18}$=H, $R^{19}$=Me) using Ligand (S,R)-2e in THF at Low Pressure Methyl pyruvate (16a, $R^{18}$=H, $R^{19}$=methyl) was hydrogenated at ambient temperature according to General Procedure A in THF at 0.69–1.38 bars gauge (10–20 psig) hydrogen using bis(1,5-cyclooctadiene)rhodium trifluoromethanesulfonate (2.3 mg; 5 μmol; 0.01 equiv) and ligand (S,R)-2e (3.1 mg; 6 μmol; 0.012 equiv) for 1 hour to afford 67% conversion to methyl S-lactate (S-17a, $R^{18}$=H, $R^{19}$=methyl) with 91.7% ee as determined by chiral GC analysis.

Example 55

Methyl Lactate (17a, $R^{18}$=H, $R^{19}$=Me) using Ligand (S,R)-2e in THF at High Pressure Methyl pyruvate (16a, $R^{18}$=H, $R^{19}$=methyl) was hydrogenated at ambient temperature according to General Procedure B in THF at 20.7 barg (300 psig) hydrogen using bis(1,5-cyclooctadiene)rhodium trifluoromethanesulfonate (2.3 mg; 5 μmol; 0.01 equiv) and ligand (S,R)-2e (3.1 mg; 6 μmol; 0.012 equiv) for 6 hours to afford 98.7% conversion to methyl S-lactate (S-17a, $R^{18}$=H, $R^{19}$=methyl) with 88.6% ee as determined by chiral GC analysis.

Example 56

Methyl Lactate (17a, $R^{18}$=H, $R^{19}$=Me) using Ligand (R,S)-1f in THF at High Pressure Methyl pyruvate (16a, $R^{18}$=H, $R^{19}$=methyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1f (3.3 mg; 6 μmol; 0.012 equiv) for 6 hours to afford 99.6% conversion to methyl R-lactate (R-17a, $R^{18}$=H, $R^{19}$=methyl) with 88.6% ee as determined by chiral GC analysis.

Example 57

Methyl Lactate (17a, $R^{18}$=H, $R^{19}$=Me) using Ligand (R,S)-1g in THF at Low Pressure Methyl pyruvate (16a, $R^{18}$=H, $R^{19}$=methyl) was hydrogenated according to General Procedure A in THF at 0.69–1.38 bars gauge (10–20 psig) hydrogen at ambient temperature using bis(1,5-cyclooctadiene)rhodium trifluoromethanesulfonate (2.3 mg; 5 μmol; 0.01 equiv) and ligand (R,S)-1g (3.7 mg; 6 μmol; 0.012 equiv) for 17 hours to afford 99% conversion to methyl R-lactate (R-17a, $R^{18}$=H, $R^{19}$=methyl) with 90.8% ee as determined by chiral GC analysis.

Example 58

Methyl Lactate (17a, $R^{18}$=H, $R^{19}$=Me) using Ligand (R,S)-1g in THF at High Pressure Methyl pyruvate (16a, $R^{18}$=H, $R^{19}$=methyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1g (3.7 mg; 6 μmol; 0.012 equiv) for 6 hours to afford 100% conversion to methyl R-lactate (R-17a, $R^{18}$=H, $R^{19}$=methyl) with 88.1% ee as determined by chiral GC analysis.

Example 59

Ethyl Lactate (17b, $R^{18}$=H, $R^{19}$=ethyl) using Ligand (R,S)-1b in THF at High Pressure Ethyl pyruvate (16b, $R^{18}$=H, $R^{19}$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 98.6% conversion to ethyl R-lactate (R-17b, $R^{18}$=H, $R^{19}$=ethyl) with 83.4% ee as determined by chiral GC analysis. The analytical properties of 17b were identical to an authentic sample.

Chiral GC [Cyclosil-B (J&W Scientific) 30 m×0.25 mm ID, film thickness 0.25 μm, 75° C. isothermal, 14 psig He]: $t_R$(R-17b) 11.40 min, $t_R$(S-17b) 13.24 min, $t_R$(16b) 7.73 min.

Example 60

Ethyl Lactate (17b, $R^{18}$=H, $R^{19}$=ethyl) using Ligand (R,S)-1d in THF at High Pressure Ethyl pyruvate (16b, $R^{18}$=H, $R^{19}$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1d (3.8 mg; 6 μmol; 0.012 equiv) for 6 hours to afford 99.8% conversion to ethyl R-lactate (R-17b, $R^{18}$=H, $R^{19}$=ethyl) with 87.8% ee as determined by chiral GC analysis.

Example 61

Ethyl Lactate (17b, $R^{18}$=H, $R^{19}$=ethyl) using Ligand (S,R)-2e in THF at High Pressure Ethyl pyruvate (16b, $R^{18}$=H, $R^9$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (S,R)-2e (3.1 mg; 6 μmol; 0.012 equiv) for 6 hours to afford 99.9% conversion to ethyl S-lactate (S-17b, $R^{18}$=H, $R^{19}$=ethyl) with 89.8% ee as determined by chiral GC analysis.

Example 62

Ethyl Lactate (17b, $R^{18}$=H, $R^{19}$=ethyl) using Ligand (R,S)-1f in THF at High Pressure Ethyl Pyruvate (16b, $R^{17}$=H, $R^{18}$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1f (3.3 mg; 6 μmol; 0.012 equiv) for 6 hours to afford 99.9% conversion to ethyl R-lactate (R-17b, $R^{18}$=H, $R^{19}$=ethyl) with 89.8% ee as determined by chiral GC analysis.

Example 63

Ethyl Lactate (17b, $R^{18}$=H, $R^{19}$=ethyl) using Ligand (R, S)-1g in THF at High Pressure Ethyl pyruvate (16b, $R^{18}$=H, $R^{19}$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1g (3.7 mg; 6 μmol; 0.012 equiv) for 6 hours to afford 99.9% conversion to ethyl R-lactate (R-17b, $R^{18}$=H, $R^{19}$=ethyl) with 90.8% ee as determined by chiral GC analysis.

Example 64

Ethyl 2-Hydroxy-4-phenylbutyrate (17c, $R^{18}$=PhCH$_2$, $R^{19}$=ethyl) using Ligand (R,S)-1b in THF at High Pressure Ethyl 2-oxo-4-phenylbutyrate (16c, $R^{18}$=PhCH$_2$, $R^{19}$=Et) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1b (3.7 mg; 6 μmol; 0.012 equiv) for 6 hours to afford 97.0% conversion to ethyl R-2-hydroxy-4-phenylbutyrate (R-17c, $R^{18}$=PhCH$_2$, $R^{19}$=ethyl) with 85.2% ee as determined by chiral GC analysis.

$^1$H NMR (CDCl$_3$) δ 7.4–7.1 (m, 5H); 4.213 (q, 1H, J=7.14 Hz); 4.15 (m, 1H); 2.77 (m, 2H); 2.12 (m, 1H); 1.96 (m, 1H); 1.286 (t, 3H, J=7.14 Hz). Chiral GC [Cyclosil-B (J&W Scientific) 30 m×0.25 mm ID, film thickness 0.25 μm, 150° C. isothermal, 18 psig He]: $t_R$(R-17c) 26.49 min, $t_R$(S-17c) 27.09 min, $t_R$($^{16}$c) 23.98 min.

Example 65

Ethyl 2-Hydroxy-4-phenylbutyrate (17c, $R^{18}$=PhCH$_2$, $R^{19}$=ethyl) using Ligand (R,S)-1c in THF at High Pressure Ethyl 2-oxo-4-phenylbutyrate (16c, $R^{18}$=PhCH$_2$, $R^{19}$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1c (3.8 mg; 6 μmol; 0.012 equiv) for 6 hours to afford 50.0% conversion to ethyl R-2-hydroxy-4-phenylbutyrate (R-17c, $R^{18}$=PhCH$_2$, $R^{19}$=ethyl) with 85.8% ee as determined by chiral GC analysis.

Example 66

Ethyl 2-Hydroxy-4-phenylbutyrate (17c, $R^{18}$=PhCH$_2$, $R^{19}$=ethyl) using Ligand (R,S)-1d in THF at High Pressure Ethyl 2-oxo-4-phenylbutyrate (16c, $R^{18}$=PhCH$_2$, $R^{19}$=Et) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1d (3.8 mg; 6 μmol; 0.012 equiv) for 6 hours to afford 98.0% conversion to ethyl R-2-hydroxy-4-phenylbutyrate (R-17c, $R^{18}$=PhCH$_2$, $R^{19}$=ethyl) with 88.6% ee as determined by chiral GC analysis.

Example 67

Ethyl 2-Hydroxy-4-phenylbutyrate (17c, $R^{18}$=PhCH$_2$, $R^{19}$=ethyl) using Ligand (S,R)-2e in THF at High Pressure Ethyl 2-oxo-4-phenylbutyrate (16c, $R^{18}$=PhCH$_2$, $R^{19}$=ethyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (S,R)-2e (3.1 mg; 6 μmol; 0.012 equiv) for 6 hours to afford 97.2% conversion to ethyl S-2-hydroxy-4-phenylbutyrate (S-17c, $R^{18}$=PhCH$_2$, $R^{19}$=ethyl) with 89.0% ee as determined by chiral GC analysis.

Example 68

Ethyl 2-Hydroxy-4-phenylbutyrate (17c, $R^{18}$=PhCH$_2$, $R^{19}$=ethyl) using Ligand (R,S)-1g in THF at Low Pressure:

Ethyl 2-oxo-4-phenylbutyrate (16c, $R^{18}$=PhCH$_2$, $R^{19}$=ethyl) was hydrogenated according to General Procedure A in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1g (3.7 mg; 6 μmol; 0.012 equiv) for 24 hours to afford 65% conversion to ethyl R-2-hydroxy-4-phenylbutyrate (R-17c, $R^{18}$=PhCH$_2$, $R^{19}$=ethyl) with 80.2% ee as determined by chiral GC analysis.

Example 69

Ethyl 2-Hydroxy-4-phenylbutyrate (17c, $R^{18}$=PhCH$_2$, $R^{19}$=ethyl) using Ligand (R,S)-1g in THF at High Pressure Ethyl 2-oxo-4-phenylbutyrate (16c, $R^{18}$=PhCH$_2$, $R^{19}$=Et) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1g (3.7 mg; 6 μmol; 0.012 equiv) for 6 hours to afford 96.6% conversion to ethyl R-2-hydroxy-4-phenylbutyrate (R-17c, $R^{18}$=PhCH$_2$, $R^{19}$=ethyl) with 92.4% ee as determined by chiral GC analysis.

Example 70

Methyl 2-Hydroxy-3-phenylpropionate (17d, $R^{18}$=Ph, $R^{19}$=methyl) using Ligand (S,R)-2e in THF at High Pressure Methyl 2-oxo-3-phenylpropionate (16d, $R^{18}$=Ph, $R^{19}$=methyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (S,R)-2e (3.1 mg; 6 μmol; 0.012 equiv) for 6 hours to afford methyl 2-hydroxy-3-phenylpropionate (17d, $R^{18}$=Ph, $R^{19}$=methyl) with 83.2% ee as determined by chiral GC analysis.

$^1$H NMR (DMSO-d$_6$) δ 7.3–7.1 (m, 5H); 5.547 (d, 1H, J=6.04 Hz); 4.22 (m, 1H); 3.584 (s, 3H); 2.923 (dd, 1H, J=5.22, 13.74 Hz); 2.289 (dd, 1H, J=8.24,13.74 Hz). Chiral GC [Cyclosil-B (J&W Scientific) 30 m×0.25 mm ID, film thickness 0.25 μm, 140° C. isothermal, 18 psig He]: $t_R$(enantiomer 1, 17d) 19.62 min, $t_R$(enantiomer 2, 17d) 21.54 min, $t_R$(16d) 18.54 min.

Example 71

Methyl 2-Hydroxy-3-phenylpropionate (17d, $R^{18}$=Ph, $R^{19}$=methyl) using Ligand (R,S)-1f in THF at High Pressure Methyl 2-oxo-3-phenylpropionate (16d, $R^{18}$=Ph, $R^{19}$=methyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1f (3.3 mg; 6 μmol; 0.012 equiv) for 6 hours to afford methyl 2-hydroxy-3-phenylpropionate (17d, $R^{18}$=Ph, $R^{19}$=methyl) with 86.0% ee as determined by chiral GC analysis.

Example 72

Methyl 2-Hydroxy-3-phenylpropionate (17d, $R^{18}$=Ph, $R^{19}$=methyl) using Ligand (R,S)-1g in THF at High Pressure Methyl 2-oxo-3-phenylpropionate (16d, $R^{18}$=Ph, $R^{19}$=methyl) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (R,S)-1g (3.7 mg; 6 μmol; 0.012 equiv) for 6 hours to afford 30% conversion to methyl 2-hydroxy-3-phenylpropionate (17d, $R^{18}$=Ph, $R^{19}$methyl) with 85.4% ee as determined by chiral GC analysis.

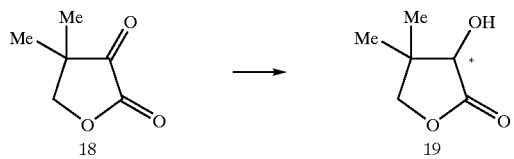

Example 73

2-Hydroxy-3,3-dimethyl-γ-butyrolactone (19) using Ligand (S,R)-2e in THF at High Pressure 2-Oxo-3,3-dimethyl-γ-butyrolactone (18) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (S,R)-2e (3.1 mg; 6 μmol; 0.012 equiv) for 6 hours to afford 99.0% conversion to 2-hydroxy-3,3-dimethyl-y-butyrolactone (19) with 95.0% ee as determined by chiral GC analysis.

$^1$H NMR (CDCl$_3$) δ 4.114 (s, 1H); 4.023 (d, 1H, J=8.52 Hz); 3.936 (d, 1H, J=8.52 Hz); 1.223 (s, 3H); 1.071 (s, 3H). Chiral GC [Cyclosil-B (J&W Scientific) 30 m×0.25 mm ID, film thickness 0.25 μm, 140° C. isothermal, 14 psig He]: $t_R$(enantiomer 1, 19) 11.18 min, $t_R$(enantiomer 2, 19) 11.66 min, $t_R$(18) 7.99 min.

Example 74

2-Hydroxy-3,3-dimethyl-γ-butyrolactone (19) using Ligand (S,R)-2f in THF at High Pressure 2-Oxo-3,3-dimethyl-y-butyrolactone (18) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (S,R)-2f (3.3 mg; 6 μmol; 0.012 equiv) for 6 hours to afford 99.6% conversion to 2-hydroxy-3,3-dimethyl-γ-butyrolactone (19) with 96.6% ee as determined by chiral GC analysis.

Example 75

2-Hydroxy-3, 3-dimethyl-γ-butyrolactone (19) using Ligand (S, R)-2g in THF

2-Oxo-3,3-dimethyl-γ-butyrolactone (18) was hydrogenated according to General Procedure B in THF at 20.7 barg (300 psig) hydrogen at ambient temperature using bis(1,5-cyclooctadiene)rhodium trifluoromethanesulfonate (2.3 mg; 5 μmol; 0.01 equiv) and ligand (S,R)-2g (3.7 mg; 6 μmol; 0.012 equiv) for 6 hours to afford 99.6% conversion to 2-hydroxy-3,3-dimethyl-γ-butyrolactone (19) with 97.2% ee as determined by chiral GC analysis.

The invention has been described in detail with particular reference to preferred embodiments thereof, but it will be understood that variations and modifications can be effected within the spirit and scope of the invention.

We claim:

1. A substantially enantiomerically pure compound having formula 1:

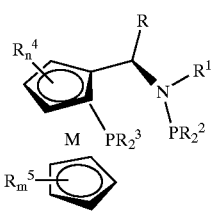

wherein

R is selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

2. A compound according to claim 1 wherein R is methyl, $R^2$ is phenyl, ethyl, isopropyl, or cyclohexyl, $R^3$ is phenyl, n and m are 0, and M is iron, ruthenium, or osmium.

3. A compound according to claim 2 where $R^1$ is hydrogen, methyl, ethyl, or n-propyl and M is iron.

4. A substantially enantiomerically pure compound having formula 2:

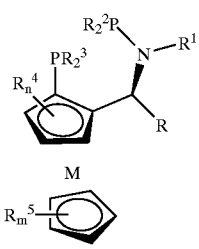

wherein

R is selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

5. A compound according to claim 4 where R is methyl, $R^2$ is phenyl, ethyl, isopropyl, or cyclohexyl, $R^3$ is phenyl, n and m are 0, and M is iron, ruthenium, or osmium.

6. A compound according to claim 5 where $R^1$ is hydrogen, methyl, ethyl, or n-propyl and M is iron.

7. A compound comprising a substantially enantiomerically pure compound defined in claim 1 in complex association with a Group VIII metal.

8. A compound according to claim 7 wherein R is methyl, $R^1$ is hydrogen, methyl, ethyl, or n-propyl, $R^2$ is phenyl, ethyl, isopropyl, or cyclohexyl, $R^3$ is phenyl, n and m are 0, and M is iron, ruthenium, or osmium and the Group VIII metal is rhodium, iridium or ruthenium.

9. A compound comprising a substantially enantiomerically pure compound defined in claim 3 in complex association with a Group VIII metal.

10. A compound according to claim 9 wherein R is methyl, $R^1$ is hydrogen, methyl, ethyl, or n-propyl, $R^2$ is phenyl, ethyl, isopropyl, or cyclohexyl, $R^3$ is phenyl, n and m are 0, and M is iron, ruthenium, or osmium and the Group VIII metal is rhodium, iridium or ruthenium.

11. A process for the preparation of a substantially enantiomerically pure compound having formula 1:

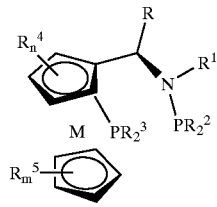

1 which comprises the steps of:

(1) contacting a dialkylamine having formula 3:

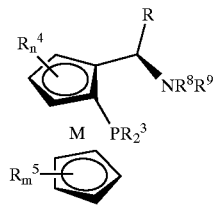

3 with a carboxylic anhydride having the formula $(R^{10}CO)_2O$ to obtain an ester compound having formula 4:

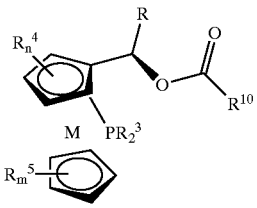

4

(2) contacting the ester produced in step (1) with an amine having the formula $H_2N$—$R^1$ to obtain an intermediate compound having formula 5:

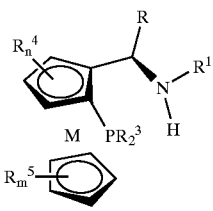

5

(3) contacting intermediate compound 5 with a halophosphine having the formula X—$P(R^2)_2$;

wherein

R, $R^8$, and $R^9$ are independently selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted or unsubstituted $C_4$–$C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;

n is 0 to 3;

m is 0 to 5;

M is selected from the metals of Groups IVB, VB, VIB, VIIB and VIII;

$R^{10}$ is a $C_1$ to $C_4$ alkyl radical; and

X is chlorine, bromine, or iodine.

12. A process according to claim 12 wherein R, $R^8$, and $R^9$ are methyl, $R^2$ is phenyl, ethyl, isopropyl, or cyclohexyl, $R^3$ is phenyl, X is chlorine or bromine, n and m are 0, and M is iron, ruthenium, or osmium.

13. A process according to claim 11 where $R^1$ is hydrogen, methyl, ethyl, or n-propyl, X is chlorine, and M is iron.

14. A process according to claim 10 wherein the carboxylic anhydride is selected from acetic, propionic, or butyric anhydride and the lower alcohol solvent is selected from methanol, ethanol, n-propanol, isopropanol, n-butanol, sec-butanol, or tert-butanol.

15. A process according to claim 14 wherein step (3) is carried out in the presence of a $C_3$–$C_{15}$ trialkylamine and a non-polar, aprotic solvent selected from aliphatic and aromatic hydrocarbons containing 6 to 10 carbon atoms, halogenated hydrocarbons containing up to about 6 carbon atoms, and cyclic and acyclic ethers containing from about 4 to 8 carbon atoms.

16. A process according to claim 15 wherein step (3) is carried out in the presence of triethylamine and toluene.

17. A process for the preparation of a substantially enantiomerically pure compound having formula 2:

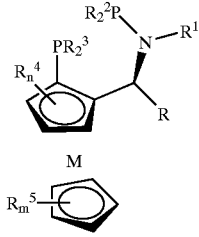

which comprises the steps of:

(1) contacting a dialkylamine having formula 6:

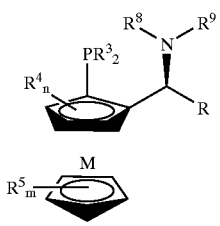

with a carboxylic anhydride having the formula $(R^{10}CO)_2O$ to obtain an ester compound having formula 7:

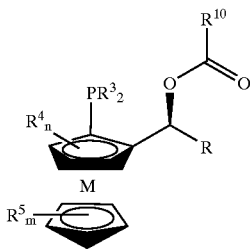

(2) contacting the ester produced in step (1) with an amine having the formula $H_2N-R^1$ to obtain an intermediate compound having formula 8:

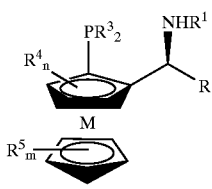

(3) contacting intermediate compound 8 with a halophosphine having the formula $X-P(R^2)_2$;

wherein

R, $R^8$, and $R^9$ are independently selected from substituted and unsubstituted, branched- and straight-chain $C_1-C_{20}$ alkyl, substituted and unsubstituted $C_3-C_8$ cycloalkyl, substituted and unsubstituted $C_6-C_{20}$ carbocyclic aryl, and substituted and unsubstituted $C_4-C_{20}$ heteroaryl wherein the heteroatoms are selected from sulfur, nitrogen, and oxygen;

$R^1$, $R^2$, $R^3$, $R^4$, and $R^5$ are independently selected from hydrogen, substituted and unsubstituted, branched- and straight-chain $C_1-C_{20}$ alkyl, substituted and unsubstituted $C_3-C_8$ cycloalkyl, substituted and unsubstituted $C_6-C_{20}$ carbocyclic aryl, and substituted and unsubstituted $C_4-C_{20}$ heteroaryl wherein the heteroatoms are selected from sulfur, nitrogen, and oxygen;

n is 0 to 3;

m is 0 to 5;

M is selected from the metals of Groups IVB, VB, VIB, VIIB and VIII;

$R^{10}$ is a $C_1$ to $C_4$ alkyl radical; and

X is chlorine, bromine, or iodine.

18. A process according to claim 17 wherein R, $R^8$, and $R^9$ are methyl, $R^2$ is phenyl, ethyl, isopropyl, or cyclohexyl, $R^3$ is phenyl, X is chlorine or bromine, n and m are 0, and M is iron, ruthenium, or osmium.

19. A process according to claim 18 wherein $R^1$ is hydrogen, methyl, ethyl, or n-propyl, X is chlorine, and M is iron.

20. A process according to claim 17 wherein the carboxylic anhydride is selected from acetic, propionic, or butyric anhydride and the lower alcohol solvent is selected from methanol, ethanol, n-propanol, isopropanol, n-butanol, sec-butanol, or tert-butanol.

21. A process according to claim 20 wherein step (3) is carried out in the presence of a $C_3-C_{15}$ trialkylamine and a non-polar, aprotic solvent selected from aliphatic and aromatic hydrocarbons containing 6 to 10 carbon atoms, halogenated hydrocarbons containing up to about 6 carbon atoms, and cyclic and acyclic ethers containing from about 4 to 8 carbon atoms.

22. A process according to claim 20 wherein step (3) is carried out in the presence of triethylamine and toluene.

23. An amino-phosphine compound having the formula

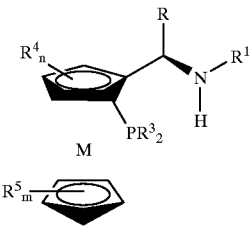

wherein

R and $R^1$ are independently selected from substituted and unsubstituted, branched- and straight-chain $C_1-C_{20}$ alkyl, substituted or unsubstituted $C_3-C_8$ cycloalkyl, substituted and unsubstituted $C_6-C_{20}$ carbocyclic aryl, and substituted and unsubstituted $C_4-C_{20}$ heteroaryl wherein the heteroatoms are selected from sulfur, nitrogen, and oxygen;

$R^3$, $R^4$, and $R^5$ are independently selected from hydrogen, substituted and unsubstituted, branched- and straight-chain $C_1-C_{20}$ alkyl, substituted and unsubstituted $C_3-C_8$ cycloalkyl, substituted and unsubstituted $C_6-C_{20}$ carbocyclic aryl, and substituted and unsubstituted $C_4-C_{20}$ heteroaryl wherein the heteroatoms are selected from sulfur, nitrogen, and oxygen;

n is 0 to 3;

m is 0 to 5; and

M is selected from the metals of Groups IVB, VB, VIB, VIIB and VIII.

24. A compound according to claim 23 wherein R is methyl, $R^1$ is methyl, ethyl, or n-propyl, $R^3$ is phenyl, n and m are 0, and M is iron, ruthenium, or osmium.

25. An amino-phosphine compound having the formula

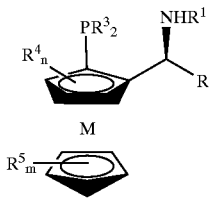

8 wherein
R and $R^1$ are independently selected from substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;
$R^3$, $R^4$, and $R^5$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen;
n is 0 to 3;
m is 0 to 5; and
M is selected from the metals of Groups IVB, VB, VIB, VIIB and VIII.

26. A compound according to claim 25 wherein R is methyl, $R^1$ is methyl, ethyl, or n-propyl, $R^3$ is phenyl, n and m are 0, and M is iron, ruthenium, or osmium.

27. A method for the enantioselective hydrogenation of a hydrogenatable compound which comprises contacting the hydrogenatable compound with hydrogen in the presence of a catalyst complex defined in any of claims 7 through 10.

28. A method according to claim 27 wherein the hydrogenatable compound contains the residue C=C(N—C=O)—C=O.

29. A method according to claim 28 wherein the hydrogenatable compound has formula 10:

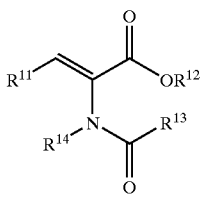

10 wherein:
$R^{11}$, $R^{12}$, and $R^{14}$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen; and
$R^{13}$ is selected from hydrogen, substituted and unsubstituted $C_1$ to $C_{20}$ alkyl, substituted and unsubstituted $C_1$ to $C_{20}$ alkoxy, substituted and unsubstituted $C_3$ to $C_8$ cycloalkyl, substituted and unsubstituted $C_3$ to $C_8$ cycloalkoxy, substituted and unsubstituted carbocyclic $C_6$ to $C_{20}$ aryl, substituted and unsubstituted carbocyclic $C_6$ to $C_{20}$ aryloxy, substituted and unsubstituted $C_4$ to $C_{20}$ heteroaryl wherein the heteroatoms are selected from sulfur, nitrogen, and oxygen and substituted and unsubstituted $C_4$ to $C_{20}$ heteroaryloxy wherein the heteroatoms are selected from sulfur, nitrogen, and oxygen; or
$R^{13}$ ands $R^{14}$ collectively represent a substituted or unsubstituted alkylene group of 1–4 chain carbon atoms forming a lactam.

30. A method according to claim 27 wherein the hydrogenatable compound has formula 14:

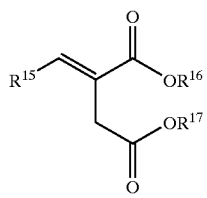

14 wherein:
$R^{15}$ is selected from hydrogen, substituted and unsubstituted, branched- and straight-chain $C_1$–$C_{20}$ alkyl, and substituted and unsubstituted $C_3$–$C_8$ cycloalkyl, and $R^{16}$ and $R^{17}$ are independently selected from hydrogen, substituted and unsubstituted, branched- and straight-chain $C_1$–$C_{20}$ alkyl, substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, and oxygen.

31. A method according to claim 27 wherein the hydrogenatable compound has formula 16:

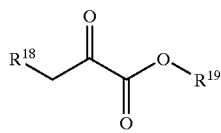

16 wherein:
$R^{18}$ and $R^{19}$ are independently selected from hydrogen, substituted and unsubstituted, branched- and straight-chain $C_1$–$C_{20}$ alkyl, and substituted and unsubstituted $C_3$–$C_8$ cycloalkyl, substituted and unsubstituted $C_6$–$C_{20}$ carbocyclic aryl, and substituted and unsubstituted $C_4$–$C_{20}$ heteroaryl wherein the heteroatoms are selected from sulfur, nitrogen, or oxygen; or
$R^{18}$ and $R^{19}$ collectively represent a substituted or unsubstituted alkylene group of 1–4 chain carbon atoms forming an α-ketolactone.

* * * * *